(12) United States Patent
He

(10) Patent No.: US 7,620,438 B2
(45) Date of Patent: Nov. 17, 2009

(54) METHOD AND SYSTEM FOR POWERING AN ELECTRONIC DEVICE

(75) Inventor: Lei He, Moraga, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 328 days.

(21) Appl. No.: 11/396,135

(22) Filed: Mar. 31, 2006

(65) Prior Publication Data

US 2007/0232877 A1    Oct. 4, 2007

(51) Int. Cl.
*A61B 5/05* (2006.01)
*A61B 5/00* (2006.01)

(52) U.S. Cl. .................. 600/345; 600/300; 600/347; 600/365

(58) Field of Classification Search .......... 600/345, 600/347, 365, 300, 301
See application file for complete search history.

(56) References Cited

U.S. PATENT DOCUMENTS

| | | |
|---|---|---|
| 3,260,656 A | 7/1966 | Ross, Jr. |
| 3,304,413 A | 2/1967 | Lehmann et al. |
| 3,581,062 A | 5/1971 | Aston |
| 3,651,318 A | 3/1972 | Czekajewski |
| 3,653,841 A | 4/1972 | Klein |
| 3,698,386 A | 10/1972 | Fried |
| 3,719,564 A | 3/1973 | Lilly, Jr. et al. |
| 3,768,014 A | 10/1973 | Smith et al. |
| 3,776,832 A | 12/1973 | Oswin et al. |
| 3,837,339 A | 9/1974 | Aisenberg et al. |
| 3,919,051 A | 11/1975 | Koch et al. |
| 3,926,760 A | 12/1975 | Allen et al. |
| 3,949,388 A | 4/1976 | Fuller |
| 3,972,320 A | 8/1976 | Kalman |
| 3,979,274 A | 9/1976 | Newman |
| 4,008,717 A | 2/1977 | Kowarski |
| 4,016,866 A | 4/1977 | Lawton |
| 4,036,749 A | 7/1977 | Anderson |
| 4,055,175 A | 10/1977 | Clemens et al. |
| 4,059,406 A | 11/1977 | Fleet |
| 4,068,536 A | 1/1978 | Rosenthal |
| 4,076,596 A | 2/1978 | Connery et al. |
| 4,098,574 A | 7/1978 | Dappen |
| 4,100,048 A | 7/1978 | Pompei et al. |
| 4,129,128 A | 12/1978 | McFarlane |
| 4,151,845 A | 5/1979 | Clemens |
| 4,154,231 A | 5/1979 | Russell |

(Continued)

FOREIGN PATENT DOCUMENTS

DE    4234553    1/1995

(Continued)

OTHER PUBLICATIONS

U.S. Appl. No. 11/537,984, He.

(Continued)

*Primary Examiner*—Patricia C Mallari
(74) *Attorney, Agent, or Firm*—Jackson & Co., LLP

(57) ABSTRACT

Methods and apparatus for providing a power supply to a device, including an inductive rechargeable power supply for a data monitoring and management system in which a high frequency magnetic field is generated to provide power supply to a rechargeable rower source such as a battery of a transmitter unit in the data monitoring and management system are provided.

25 Claims, 6 Drawing Sheets

U.S. PATENT DOCUMENTS

| | | |
|---|---|---|
| 4,168,205 A | 9/1979 | Danninger et al. |
| 4,172,770 A | 10/1979 | Semersky et al. |
| 4,178,916 A | 12/1979 | McNamara |
| 4,206,755 A | 6/1980 | Klein |
| 4,224,125 A | 9/1980 | Nakamura et al. |
| 4,240,438 A | 12/1980 | Updike et al. |
| 4,240,889 A | 12/1980 | Yoda et al. |
| 4,245,634 A | 1/1981 | Albisser et al. |
| 4,247,297 A | 1/1981 | Berti et al. |
| 4,271,449 A | 6/1981 | Grogan |
| 4,318,784 A | 3/1982 | Higgins et al. |
| 4,327,725 A | 5/1982 | Cortese et al. |
| 4,331,869 A | 5/1982 | Rollo |
| 4,340,458 A | 7/1982 | Lerner et al. |
| 4,344,438 A | 8/1982 | Schultz |
| 4,349,728 A | 9/1982 | Phillips et al. |
| 4,352,960 A | 10/1982 | Dormer et al. |
| 4,356,074 A | 10/1982 | Johnson |
| 4,365,637 A | 12/1982 | Johnson |
| 4,366,033 A | 12/1982 | Richter et al. |
| 4,375,399 A | 3/1983 | Havas et al. |
| 4,376,312 A * | 3/1983 | Robinson et al. ............ 623/3.21 |
| 4,384,586 A | 5/1983 | Christiansen |
| 4,390,621 A | 6/1983 | Bauer |
| 4,392,933 A | 7/1983 | Nakamura et al. |
| 4,401,122 A | 8/1983 | Clark, Jr. |
| 4,404,066 A | 9/1983 | Johnson |
| 4,407,959 A | 10/1983 | Tsuji et al. |
| 4,417,588 A | 11/1983 | Houghton et al. |
| 4,418,148 A | 11/1983 | Oberhardt |
| 4,420,564 A | 12/1983 | Tsuji et al. |
| 4,425,920 A | 1/1984 | Bourland et al. |
| 4,427,004 A | 1/1984 | Miller et al. |
| 4,427,770 A | 1/1984 | Chen et al. |
| 4,431,004 A | 2/1984 | Bessman et al. |
| 4,436,094 A | 3/1984 | Cerami |
| 4,440,175 A | 4/1984 | Wilkins |
| 4,444,892 A | 4/1984 | Malmros |
| 4,450,842 A | 5/1984 | Zick et al. |
| 4,458,686 A | 7/1984 | Clark, Jr. |
| 4,461,691 A | 7/1984 | Frank |
| 4,467,811 A | 8/1984 | Clark, Jr. |
| 4,469,110 A | 9/1984 | Slama |
| 4,477,314 A | 10/1984 | Richter et al. |
| 4,478,976 A | 10/1984 | Goertz et al. |
| 4,483,924 A | 11/1984 | Tsuji et al. |
| 4,484,987 A | 11/1984 | Gough |
| 4,494,950 A | 1/1985 | Fischell |
| 4,509,531 A | 4/1985 | Ward |
| 4,512,348 A | 4/1985 | Uchigaki et al. |
| 4,522,690 A | 6/1985 | Venkatsetty |
| 4,524,114 A | 6/1985 | Samuels et al. |
| 4,526,661 A | 7/1985 | Steckhan et al. |
| 4,527,240 A | 7/1985 | Kvitash |
| 4,534,356 A | 8/1985 | Papadakis |
| 4,538,616 A | 9/1985 | Rogoff |
| 4,543,955 A | 10/1985 | Schroeppel |
| 4,545,382 A | 10/1985 | Higgins et al. |
| 4,552,840 A | 11/1985 | Riffer |
| 4,560,534 A | 12/1985 | Kung et al. |
| 4,569,589 A | 2/1986 | Neufeld |
| 4,571,292 A | 2/1986 | Liu et al. |
| 4,573,994 A | 3/1986 | Fischell et al. |
| 4,581,336 A | 4/1986 | Malloy et al. |
| 4,595,011 A | 6/1986 | Phillips |
| 4,595,479 A | 6/1986 | Kimura et al. |
| 4,619,754 A | 10/1986 | Niki et al. |
| 4,619,793 A | 10/1986 | Lee |
| 4,627,445 A | 12/1986 | Garcia et al. |
| 4,627,908 A | 12/1986 | Miller |
| 4,633,878 A | 1/1987 | Bombardien |
| 4,633,881 A | 1/1987 | Moore et al. |
| 4,637,403 A | 1/1987 | Garcia et al. |
| 4,648,408 A | 3/1987 | Hutcheson et al. |
| 4,650,547 A | 3/1987 | Gough |
| 4,653,513 A | 3/1987 | Dombrowski |
| 4,654,197 A | 3/1987 | Lilja et al. |
| 4,655,880 A | 4/1987 | Liu |
| 4,655,885 A | 4/1987 | Hill et al. |
| 4,658,463 A | 4/1987 | Sugita et al. |
| 4,671,288 A | 6/1987 | Gough |
| 4,674,652 A | 6/1987 | Aten et al. |
| 4,679,562 A | 7/1987 | Luksha |
| 4,680,268 A | 7/1987 | Clark, Jr. |
| 4,682,602 A | 7/1987 | Prohaska |
| 4,684,537 A | 8/1987 | Graetzel et al. |
| 4,685,463 A | 8/1987 | Williams |
| 4,686,624 A | 8/1987 | Blum et al. |
| 4,703,756 A | 11/1987 | Gough et al. |
| 4,711,245 A | 12/1987 | Higgins et al. |
| 4,717,673 A | 1/1988 | Wrighton et al. |
| 4,721,601 A | 1/1988 | Wrighton et al. |
| 4,721,677 A | 1/1988 | Clark, Jr. |
| 4,726,378 A | 2/1988 | Kaplan |
| 4,726,716 A | 2/1988 | McGuire |
| 4,731,726 A | 3/1988 | Allen, III |
| 4,749,985 A | 6/1988 | Corsberg |
| 4,750,496 A | 6/1988 | Reinhart |
| 4,757,022 A | 7/1988 | Shults et al. |
| 4,758,323 A | 7/1988 | Davis et al. |
| 4,759,371 A | 7/1988 | Franetzki |
| 4,759,828 A | 7/1988 | Young et al. |
| 4,764,416 A | 8/1988 | Ueyama et al. |
| 4,776,944 A | 10/1988 | Janata et al. |
| 4,777,953 A | 10/1988 | Ash et al. |
| 4,779,618 A | 10/1988 | Mund et al. |
| 4,781,798 A | 11/1988 | Gough |
| 4,784,736 A | 11/1988 | Lonsdale et al. |
| 4,795,707 A | 1/1989 | Niiyama et al. |
| 4,796,634 A | 1/1989 | Huntsman et al. |
| 4,803,625 A | 2/1989 | Fu et al. |
| 4,805,624 A | 2/1989 | Yao et al. |
| 4,813,424 A | 3/1989 | Wilkins |
| 4,815,469 A | 3/1989 | Cohen et al. |
| 4,820,399 A | 4/1989 | Senda et al. |
| 4,822,337 A | 4/1989 | Newhouse et al. |
| 4,830,959 A | 5/1989 | McNeil et al. |
| 4,832,797 A | 5/1989 | Vadgama et al. |
| 4,835,372 A | 5/1989 | Gombrich et al. |
| RE32,947 E | 6/1989 | Dormer et al. |
| 4,837,049 A | 6/1989 | Byers et al. |
| 4,840,893 A | 6/1989 | Hill et al. |
| RE32,974 E | 7/1989 | Porat et al. |
| 4,844,076 A | 7/1989 | Lesho et al. |
| 4,845,035 A | 7/1989 | Fanta et al. |
| 4,848,351 A | 7/1989 | Finch |
| 4,854,322 A | 8/1989 | Ash et al. |
| 4,856,340 A | 8/1989 | Garrison |
| 4,857,713 A | 8/1989 | Brown |
| 4,858,617 A | 8/1989 | Sanders |
| 4,870,561 A | 9/1989 | Love et al. |
| 4,871,351 A | 10/1989 | Feingold |
| 4,871,440 A | 10/1989 | Nagata et al. |
| 4,874,499 A | 10/1989 | Smith et al. |
| 4,874,500 A | 10/1989 | Madou et al. |
| 4,890,620 A | 1/1990 | Gough |
| 4,890,621 A | 1/1990 | Hakky |
| 4,894,137 A | 1/1990 | Takizawa et al. |
| 4,897,162 A | 1/1990 | Lewandowski et al. |
| 4,897,173 A | 1/1990 | Nankai et al. |
| 4,899,839 A | 2/1990 | Dessertine et al. |
| 4,909,908 A | 3/1990 | Ross et al. |
| 4,911,794 A | 3/1990 | Parce et al. |
| 4,917,800 A | 4/1990 | Lonsdale et al. |

| Patent No. | Date | Inventor | Patent No. | Date | Inventor |
|---|---|---|---|---|---|
| 4,919,141 A | 4/1990 | Zier et al. | 5,126,247 A | 6/1992 | Palmer et al. |
| 4,919,767 A | 4/1990 | Vadgama et al. | 5,130,009 A | 7/1992 | Marsoner et al. |
| 4,920,969 A | 5/1990 | Suzuki | 5,133,856 A | 7/1992 | Yamaguchi et al. |
| 4,920,977 A | 5/1990 | Haynes | 5,134,391 A | 7/1992 | Okada |
| 4,923,586 A | 5/1990 | Katayama et al. | 5,135,003 A | 8/1992 | Souma |
| 4,925,268 A | 5/1990 | Iyer et al. | 5,139,023 A | 8/1992 | Stanley et al. |
| 4,927,516 A | 5/1990 | Yamaguchi et al. | 5,140,393 A | 8/1992 | Hijikihigawa et al. |
| 4,931,795 A | 6/1990 | Gord | 5,141,868 A | 8/1992 | Shanks et al. |
| 4,934,369 A | 6/1990 | Maxwell | 5,161,532 A | 11/1992 | Joseph |
| 4,935,105 A | 6/1990 | Churchouse | 5,165,407 A | 11/1992 | Wilson et al. |
| 4,935,345 A | 6/1990 | Guibeau et al. | 5,168,046 A | 12/1992 | Hamamoto et al. |
| 4,936,956 A | 6/1990 | Wrighton | 5,174,291 A | 12/1992 | Schoonen et al. |
| 4,938,860 A | 7/1990 | Wogoman | 5,176,644 A | 1/1993 | Srisathapat et al. |
| 4,942,127 A | 7/1990 | Wada et al. | 5,176,662 A | 1/1993 | Bartholomew et al. |
| 4,944,299 A | 7/1990 | Silvian | 5,182,707 A | 1/1993 | Cooper et al. |
| 4,945,045 A | 7/1990 | Forrest et al. | 5,184,359 A | 2/1993 | Tsukamura et al. |
| 4,950,378 A | 8/1990 | Nagara | 5,185,256 A | 2/1993 | Nankai et al. |
| 4,953,552 A | 9/1990 | DeMarzo | 5,190,041 A | 3/1993 | Palti |
| 4,954,129 A | 9/1990 | Giuliani et al. | 5,192,415 A | 3/1993 | Yoshioka et al. |
| 4,957,115 A | 9/1990 | Selker | 5,192,416 A | 3/1993 | Wang et al. |
| 4,958,632 A | 9/1990 | Duggan | 5,193,539 A | 3/1993 | Schulman et al. |
| 4,968,400 A | 11/1990 | Shimomura et al. | 5,193,540 A | 3/1993 | Schulman et al. |
| 4,969,468 A | 11/1990 | Byers et al. | 5,197,322 A | 3/1993 | Indravudh |
| 4,970,145 A | 11/1990 | Bennetto et al. | 5,198,367 A | 3/1993 | Aizawa et al. |
| 4,974,929 A | 12/1990 | Curry | 5,200,051 A | 4/1993 | Cozzette et al. |
| 4,979,509 A | 12/1990 | Hakky | 5,202,261 A | 4/1993 | Musho et al. |
| 4,986,271 A | 1/1991 | Wilkins | 5,205,920 A | 4/1993 | Oyama et al. |
| 4,990,845 A | 2/1991 | Gord | 5,206,145 A | 4/1993 | Cattell |
| 4,991,582 A | 2/1991 | Byers et al. | 5,208,154 A | 5/1993 | Weaver et al. |
| 4,994,068 A | 2/1991 | Hufnagie | 5,209,229 A | 5/1993 | Gilli |
| 4,994,167 A | 2/1991 | Shults et al. | 5,215,887 A | 6/1993 | Saito |
| 4,995,402 A | 2/1991 | Smith et al. | 5,216,597 A | 6/1993 | Beckers |
| 5,000,180 A | 3/1991 | Kuypers et al. | 5,217,442 A | 6/1993 | Davis |
| 5,001,054 A | 3/1991 | Wagner | 5,217,595 A | 6/1993 | Smith et al. |
| 5,002,054 A | 3/1991 | Ash et al. | 5,227,042 A | 7/1993 | Zawodzinski et al. |
| 5,007,427 A | 4/1991 | Suzuki et al. | 5,229,282 A | 7/1993 | Yoshioka et al. |
| 5,016,172 A | 5/1991 | Dessertine | 5,246,867 A | 9/1993 | Lakowicz et al. |
| 5,016,201 A | 5/1991 | Bryan et al. | 5,250,439 A | 10/1993 | Musho et al. |
| 5,019,974 A | 5/1991 | Beckers | 5,251,126 A | 10/1993 | Kahn et al. |
| 5,034,192 A | 7/1991 | Wrighton et al. | 5,257,971 A | 11/1993 | Lord et al. |
| 5,035,860 A | 7/1991 | Kleingeld et al. | 5,257,980 A | 11/1993 | Van Antwerp et al. |
| 5,036,860 A | 8/1991 | Leigh et al. | 5,261,401 A | 11/1993 | Baker et al. |
| 5,036,861 A | 8/1991 | Sembrowich et al. | 5,262,035 A | 11/1993 | Gregg et al. |
| 5,037,527 A | 8/1991 | Hayashi et al. | 5,262,305 A | 11/1993 | Heller et al. |
| 5,049,487 A | 9/1991 | Phillips et al. | 5,264,103 A | 11/1993 | Yoshioka et al. |
| 5,050,612 A | 9/1991 | Matsumura | 5,264,104 A | 11/1993 | Gregg et al. |
| 5,055,171 A | 10/1991 | Peck | 5,264,105 A | 11/1993 | Gregg et al. |
| 5,058,592 A | 10/1991 | Whisler | 5,264,106 A | 11/1993 | McAleer et al. |
| 5,063,081 A | 11/1991 | Cozzette et al. | 5,265,888 A | 11/1993 | Yamamoto et al. |
| 5,068,536 A | 11/1991 | Rosenthal | 5,266,179 A | 11/1993 | Nankai et al. |
| 5,070,535 A | 12/1991 | Hochmair et al. | 5,269,212 A | 12/1993 | Peters et al. |
| 5,073,500 A | 12/1991 | Saito et al. | 5,271,815 A | 12/1993 | Wong |
| 5,077,476 A | 12/1991 | Rosenthal | 5,272,060 A | 12/1993 | Hamamoto et al. |
| 5,078,854 A | 1/1992 | Burgess et al. | 5,275,159 A | 1/1994 | Griebel |
| 5,082,550 A | 1/1992 | Rishpon et al. | 5,278,079 A | 1/1994 | Gubinski et al. |
| 5,082,786 A | 1/1992 | Nakamoto | 5,279,294 A | 1/1994 | Anderson et al. |
| 5,084,828 A | 1/1992 | Kaufman et al. | 5,282,950 A | 2/1994 | Dietze et al. |
| 5,089,112 A | 2/1992 | Skotheim et al. | 5,284,156 A | 2/1994 | Schramm et al. |
| 5,094,951 A | 3/1992 | Rosenberg | 5,285,792 A | 2/1994 | Sjoquist et al. |
| 5,095,904 A | 3/1992 | Seligman et al. | 5,286,362 A | 2/1994 | Hoenes et al. |
| 5,096,560 A | 3/1992 | Takai et al. | 5,286,364 A | 2/1994 | Yacynych et al. |
| 5,096,836 A | 3/1992 | Macho et al. | 5,288,636 A | 2/1994 | Pollmann et al. |
| 5,101,814 A | 4/1992 | Palti | 5,291,887 A | 3/1994 | Stanley et al. |
| 5,106,365 A | 4/1992 | Hernandez | 5,293,546 A | 3/1994 | Tadros et al. |
| 5,108,564 A | 4/1992 | Szuminsky et al. | 5,293,877 A | 3/1994 | O'Hara et al. |
| 5,109,850 A | 5/1992 | Blanco et al. | 5,299,571 A | 4/1994 | Mastrototaro |
| 5,111,539 A | 5/1992 | Hiruta et al. | 5,304,468 A | 4/1994 | Phillips et al. |
| 5,111,818 A | 5/1992 | Suzuji et al. | 5,307,263 A | 4/1994 | Brown |
| 5,114,678 A | 5/1992 | Crawford et al. | 5,309,919 A | 5/1994 | Snell et al. |
| 5,120,420 A | 6/1992 | Nankai et al. | 5,310,885 A | 5/1994 | Maier et al. |
| 5,120,421 A | 6/1992 | Glass et al. | 5,320,098 A | 6/1994 | Davidson |
| 5,122,925 A | 6/1992 | Inpyn | 5,320,725 A | 6/1994 | Gregg et al. |
| 5,126,034 A | 6/1992 | Carter et al. | 5,322,063 A | 6/1994 | Allen et al. |

| | | | | | |
|---|---|---|---|---|---|
| 5,324,303 A | 6/1994 | Strong et al. | 5,514,253 A | 5/1996 | Davis et al. |
| 5,324,316 A | 6/1994 | Schulman et al. | 5,514,718 A | 5/1996 | Lewis et al. |
| 5,326,449 A | 7/1994 | Cunningham | 5,518,006 A | 5/1996 | Mawhirt et al. |
| 5,337,258 A | 8/1994 | Dennis | 5,520,787 A | 5/1996 | Hanagan et al. |
| 5,337,747 A | 8/1994 | Neftei | 5,522,865 A | 6/1996 | Schulman et al. |
| 5,340,722 A | 8/1994 | Wolfbeis et al. | 5,525,511 A | 6/1996 | D'Costa |
| 5,342,789 A | 8/1994 | Chick et al. | 5,526,120 A | 6/1996 | Jina et al. |
| 5,352,348 A | 10/1994 | Young et al. | 5,527,307 A | 6/1996 | Srisathapat et al. |
| 5,356,348 A | 10/1994 | Bellio et al. | 5,529,676 A | 6/1996 | Maley et al. |
| 5,356,786 A | 10/1994 | Heller et al. | 5,531,878 A | 7/1996 | Vadgama et al. |
| 5,358,514 A | 10/1994 | Schulman et al. | 5,538,511 A | 7/1996 | Van Antwerp et al. |
| 5,360,404 A | 11/1994 | Novacek et al. | 5,545,152 A | 8/1996 | Funderburk et al. |
| 5,364,797 A | 11/1994 | Olson et al. | 5,545,191 A | 8/1996 | Mann et al. |
| 5,366,609 A | 11/1994 | White et al. | 5,549,113 A | 8/1996 | Halleck et al. |
| 5,368,028 A | 11/1994 | Palti | 5,549,115 A | 8/1996 | Morgan et al. |
| 5,370,622 A | 12/1994 | Livingston et al. | 5,552,027 A | 9/1996 | Birkle et al. |
| 5,371,687 A | 12/1994 | Holmes, II et al. | 5,554,166 A | 9/1996 | Lange et al. |
| 5,372,133 A | 12/1994 | Hogen Esch | 5,556,524 A | 9/1996 | Albers |
| 5,372,427 A | 12/1994 | Padovani et al. | 5,560,357 A | 10/1996 | Faupei et al. |
| 5,376,070 A | 12/1994 | Purvis et al. | 5,562,713 A | 10/1996 | Silvian |
| 5,376,251 A | 12/1994 | Kaneko et al. | 5,565,085 A | 10/1996 | Ikeda et al. |
| 5,377,258 A | 12/1994 | Bro | 5,567,302 A | 10/1996 | Song et al. |
| 5,378,628 A | 1/1995 | Gratzel et al. | 5,568,806 A | 10/1996 | Cheney, II et al. |
| 5,379,238 A | 1/1995 | Stark | 5,569,186 A | 10/1996 | Lord et al. |
| 5,380,422 A | 1/1995 | Negishis et al. | 5,569,212 A | 10/1996 | Brown |
| 5,382,346 A | 1/1995 | Uenoyama et al. | 5,573,647 A | 11/1996 | Maley et al. |
| 5,387,327 A | 2/1995 | Khan | 5,575,895 A | 11/1996 | Ikeda et al. |
| 5,390,671 A | 2/1995 | Lord et al. | 5,580,527 A | 12/1996 | Bell et al. |
| 5,391,250 A | 2/1995 | Cheney, II et al. | 5,580,794 A | 12/1996 | Allen |
| 5,393,903 A | 2/1995 | Gratzel et al. | 5,582,184 A | 12/1996 | Erickson et al. |
| 5,395,504 A | 3/1995 | Saurer et al. | 5,582,697 A | 12/1996 | Ikeda et al. |
| 5,399,823 A | 3/1995 | McCusker | 5,582,698 A | 12/1996 | Flaherty et al. |
| 5,400,782 A | 3/1995 | Beaubiah | 5,584,813 A | 12/1996 | Livingston et al. |
| 5,408,999 A | 4/1995 | Singh et al. | 5,586,553 A | 12/1996 | Halili et al. |
| 5,410,471 A | 4/1995 | Alyfuku et al. | 5,589,326 A | 12/1996 | Deng et al. |
| 5,410,474 A | 4/1995 | Fox | 5,593,852 A | 1/1997 | Heller et al. |
| 5,411,647 A | 5/1995 | Johnson et al. | 5,594,906 A | 1/1997 | Holmes, II et al. |
| 5,413,690 A | 5/1995 | Kost et al. | 5,596,150 A | 1/1997 | Arndy et al. |
| 5,420,379 A | 5/1995 | Zank et al. | 5,596,994 A | 1/1997 | Bro |
| 5,422,246 A | 6/1995 | Koopal et al. | 5,601,435 A | 2/1997 | Quy |
| 5,431,160 A | 7/1995 | Wilkins | 5,601,694 A | 2/1997 | Maley et al. |
| 5,431,691 A | 7/1995 | Snell et al. | 5,605,152 A | 2/1997 | Slate et al. |
| 5,431,921 A | 7/1995 | Thombre | 5,609,575 A | 3/1997 | Larson et al. |
| 5,433,710 A | 7/1995 | Van Antwerp et al. | 5,611,900 A | 3/1997 | Worden et al. |
| 5,437,973 A | 8/1995 | Vadgama et al. | 5,615,671 A | 4/1997 | Schoonen et al. |
| 5,437,999 A | 8/1995 | Dieboid et al. | 5,616,222 A | 4/1997 | Maley et al. |
| 5,445,611 A | 8/1995 | Eppstein et al. | 5,617,851 A | 4/1997 | Lipkovker |
| 5,445,920 A | 8/1995 | Saito | 5,623,925 A | 4/1997 | Swenson et al. |
| 5,456,692 A | 10/1995 | Smith, Jr. et al. | 5,628,309 A | 5/1997 | Brown |
| 5,456,940 A | 10/1995 | Funderburk | 5,628,310 A | 5/1997 | Rao et al. |
| 5,458,140 A | 10/1995 | Eppstein et al. | 5,628,890 A | 5/1997 | Carter et al. |
| 5,460,618 A | 10/1995 | Harreld | 5,629,981 A | 5/1997 | Nerlikar |
| 5,462,525 A | 10/1995 | Srisathapat et al. | 5,637,095 A | 6/1997 | Nason et al. |
| 5,462,645 A | 10/1995 | Albery et al. | 5,640,764 A | 6/1997 | Strojnik |
| 5,466,218 A | 11/1995 | Srisathapat et al. | 5,640,954 A | 6/1997 | Pfeiffer et al. |
| 5,469,846 A | 11/1995 | Khan | 5,643,212 A | 7/1997 | Coutre et al. |
| 5,472,317 A | 12/1995 | Field et al. | 5,647,853 A | 7/1997 | Feldmann et al. |
| 5,476,460 A | 12/1995 | Montalvo | 5,650,062 A | 7/1997 | Ikeda et al. |
| 5,477,855 A | 12/1995 | Schindler et al. | 5,651,767 A | 7/1997 | Schulman et al. |
| 5,482,473 A | 1/1996 | Lord et al. | 5,651,869 A | 7/1997 | Yoshioka et al. |
| 5,484,404 A | 1/1996 | Schulman et al. | 5,653,239 A | 8/1997 | Pompei et al. |
| 5,487,751 A | 1/1996 | Radons et al. | 5,660,163 A | 8/1997 | Schulman et al. |
| 5,491,474 A | 2/1996 | Suni et al. | 5,665,065 A | 9/1997 | Colman et al. |
| 5,494,562 A | 2/1996 | Maley et al. | 5,665,222 A | 9/1997 | Heller et al. |
| 5,496,453 A | 3/1996 | Uenoyama et al. | 5,667,983 A | 9/1997 | Abel et al. |
| 5,497,772 A | 3/1996 | Schulman et al. | 5,670,031 A | 9/1997 | Hintsche et al. |
| 5,501,956 A | 3/1996 | Wada et al. | 5,678,571 A | 10/1997 | Brown |
| 5,505,709 A | 4/1996 | Funderburk | 5,679,690 A | 10/1997 | Andre et al. |
| 5,505,713 A | 4/1996 | Van Antwerp et al. | 5,680,858 A | 10/1997 | Hansen et al. |
| 5,507,288 A | 4/1996 | Bocker et al. | 5,682,233 A | 10/1997 | Brinda |
| 5,508,171 A | 4/1996 | Walling et al. | 5,686,717 A | 11/1997 | Knowles et al. |
| 5,509,410 A | 4/1996 | Hill et al. | 5,695,623 A | 12/1997 | Michel et al. |
| 5,514,103 A | 5/1996 | Srisathapat et al. | 5,695,949 A | 12/1997 | Galen et al. |

| Patent | Date | Inventor |
|---|---|---|
| 5,701,894 A | 12/1997 | Cherry et al. |
| 5,704,922 A | 1/1998 | Brown |
| 5,707,502 A | 1/1998 | McCaffrey et al. |
| 5,708,247 A | 1/1998 | McAleer et al. |
| 5,710,630 A | 1/1998 | Essenpreis et al. |
| 5,711,001 A | 1/1998 | Bussan et al. |
| 5,711,297 A | 1/1998 | Iliff et al. |
| 5,711,861 A | 1/1998 | Ward et al. |
| 5,711,862 A | 1/1998 | Sakoda et al. |
| 5,711,868 A | 1/1998 | Maley et al. |
| 5,718,234 A | 2/1998 | Warden et al. |
| 5,720,733 A | 2/1998 | Brown |
| 5,720,862 A | 2/1998 | Hamamoto et al. |
| 5,721,783 A | 2/1998 | Anderson |
| 5,722,397 A | 3/1998 | Eppstein |
| 5,727,548 A | 3/1998 | Hill et al. |
| 5,730,124 A | 3/1998 | Yamauchi |
| 5,730,654 A | 3/1998 | Brown |
| 5,735,273 A | 4/1998 | Kurnik et al. |
| 5,735,285 A | 4/1998 | Albert et al. |
| 5,741,211 A | 4/1998 | Renirie et al. |
| 5,741,688 A | 4/1998 | Oxenboll et al. |
| 5,746,217 A | 5/1998 | Erickson et al. |
| 5,750,926 A | 5/1998 | Schulman et al. |
| 5,769,877 A * | 6/1998 | Barreras, Sr. ............... 607/61 |
| 5,770,028 A | 6/1998 | Maley et al. |
| 5,771,001 A | 6/1998 | Cobb |
| 5,771,890 A | 6/1998 | Tamada |
| 5,772,586 A | 6/1998 | Heinonen et al. |
| 5,777,060 A | 7/1998 | Van Antwerp |
| 5,779,665 A | 7/1998 | Mastrototaro et al. |
| 5,782,814 A | 7/1998 | Brown et al. |
| 5,785,681 A | 7/1998 | Indravudh |
| 5,786,439 A | 7/1998 | Van Antwerp et al. |
| 5,786,584 A | 7/1998 | Button et al. |
| 5,788,678 A | 8/1998 | Van Antwerp |
| 5,791,344 A | 8/1998 | Schulman et al. |
| 5,792,117 A | 8/1998 | Brown |
| 5,800,420 A | 9/1998 | Gross et al. |
| 5,804,048 A | 9/1998 | Wong et al. |
| 5,807,315 A | 9/1998 | Van Antwerp et al. |
| 5,807,375 A | 9/1998 | Gross et al. |
| 5,814,599 A | 9/1998 | Mitragotri et al. |
| 5,820,551 A | 10/1998 | Hill et al. |
| 5,820,570 A | 10/1998 | Erickson et al. |
| 5,820,622 A | 10/1998 | Gross et al. |
| 5,822,715 A | 10/1998 | Worthington et al. |
| 5,825,488 A | 10/1998 | Kohl et al. |
| 5,827,179 A | 10/1998 | Lichter et al. |
| 5,827,183 A | 10/1998 | Kurnik et al. |
| 5,827,184 A | 10/1998 | Netherly et al. |
| 5,828,943 A | 10/1998 | Brown |
| 5,830,341 A | 11/1998 | Gilmartin |
| 5,832,448 A | 11/1998 | Brown |
| 5,834,224 A | 11/1998 | Ruger et al. |
| 5,837,454 A | 11/1998 | Cozzette et al. |
| 5,837,546 A | 11/1998 | Allen et al. |
| 5,840,020 A | 11/1998 | Heinonen et al. |
| 5,842,983 A | 12/1998 | Abel et al. |
| 5,843,140 A | 12/1998 | Strojnik |
| 5,846,702 A | 12/1998 | Deng et al. |
| 5,846,744 A | 12/1998 | Athey et al. |
| 5,851,197 A | 12/1998 | Marano et al. |
| 5,854,078 A | 12/1998 | Asher et al. |
| 5,854,189 A | 12/1998 | Kruse et al. |
| 5,857,967 A | 1/1999 | Frid et al. |
| 5,857,983 A | 1/1999 | Douglas et al. |
| 5,860,917 A | 1/1999 | Comanor et al. |
| 5,872,713 A | 2/1999 | Douglas et al. |
| 5,876,484 A | 3/1999 | Raskin et al. |
| 5,879,163 A | 3/1999 | Brown et al. |
| 5,879,311 A | 3/1999 | Duchon et al. |
| 5,880,829 A | 3/1999 | Kauhaniemi et al. |
| 5,882,494 A | 3/1999 | Van Antwerp |
| 5,885,211 A | 3/1999 | Eppstein et al. |
| 5,887,133 A | 3/1999 | Brown et al. |
| 5,897,493 A | 4/1999 | Brown |
| 5,898,025 A | 4/1999 | Burg et al. |
| 5,899,855 A | 5/1999 | Brown |
| 5,913,310 A | 6/1999 | Brown |
| 5,917,346 A | 6/1999 | Gord |
| 5,918,603 A | 7/1999 | Brown |
| 5,925,021 A | 7/1999 | Castellano et al. |
| 5,931,791 A | 8/1999 | Saltzstein et al. |
| 5,933,136 A | 8/1999 | Brown |
| 5,940,801 A | 8/1999 | Brown |
| 5,942,979 A | 8/1999 | Luppino |
| 5,945,345 A | 8/1999 | Blatt et al. |
| 5,947,921 A | 9/1999 | Johnson et al. |
| 5,948,512 A | 9/1999 | Kubota et al. |
| 5,950,632 A | 9/1999 | Reber et al. |
| 5,951,300 A | 9/1999 | Brown |
| 5,951,492 A | 9/1999 | Douglas et al. |
| 5,951,521 A | 9/1999 | Mastrototaro et al. |
| 5,951,836 A | 9/1999 | McAleer et al. |
| 5,954,643 A | 9/1999 | VanAntwerp |
| 5,954,685 A | 9/1999 | Tierny |
| 5,954,700 A | 9/1999 | Kovelman |
| 5,956,501 A | 9/1999 | Brown |
| 5,957,854 A | 9/1999 | Besson et al. |
| 5,957,890 A | 9/1999 | Mann et al. |
| 5,957,958 A | 9/1999 | Schulman et al. |
| 5,960,403 A | 9/1999 | Brown |
| 5,961,451 A | 10/1999 | Reber et al. |
| 5,964,993 A | 10/1999 | Blubaugh, Jr. et al. |
| 5,965,380 A | 10/1999 | Heller et al. |
| 5,968,839 A | 10/1999 | Blatt et al. |
| 5,971,922 A | 10/1999 | Arita et al. |
| 5,971,941 A | 10/1999 | Simons et al. |
| 5,974,124 A | 10/1999 | Schlueter, Jr. et al. |
| 5,977,476 A | 11/1999 | Guha et al. |
| 5,981,294 A | 11/1999 | Blatt et al. |
| 5,989,409 A | 11/1999 | Kurnik et al. |
| 5,994,476 A | 11/1999 | Shin et al. |
| 5,995,860 A | 11/1999 | Sun et al. |
| 5,997,476 A | 12/1999 | Brown |
| 5,999,848 A | 12/1999 | Gord et al. |
| 5,999,849 A | 12/1999 | Gord et al. |
| 6,001,067 A | 12/1999 | Shults et al. |
| 6,002,954 A | 12/1999 | Van Antwerp et al. |
| 6,002,961 A | 12/1999 | Mitragotri et al. |
| 6,004,441 A | 12/1999 | Fujiwara et al. |
| 6,011,984 A | 1/2000 | Van Antwerp et al. |
| 6,014,577 A | 1/2000 | Henning |
| 6,018,678 A | 1/2000 | Mitragotri et al. |
| 6,023,629 A | 2/2000 | Tamada |
| 6,024,699 A | 2/2000 | Surwit et al. |
| 6,026,320 A | 2/2000 | Carlson et al. |
| 6,027,459 A | 2/2000 | Shain et al. |
| 6,027,692 A | 2/2000 | Galen et al. |
| 6,032,059 A | 2/2000 | Henning et al. |
| 6,032,199 A | 2/2000 | Lim et al. |
| 6,033,866 A | 3/2000 | Guo et al. |
| 6,035,237 A | 3/2000 | Schulman et al. |
| 6,040,194 A | 3/2000 | Chick et al. |
| 6,041,253 A | 3/2000 | Kost et al. |
| 6,043,437 A | 3/2000 | Schulman et al. |
| 6,049,727 A | 4/2000 | Crothall |
| 6,056,718 A | 5/2000 | Funderburk et al. |
| 6,063,459 A | 5/2000 | Velte |
| 6,066,243 A | 5/2000 | Anderson et al. |
| 6,067,474 A | 5/2000 | Schulman et al. |
| 6,068,615 A | 5/2000 | Brown et al. |
| 6,071,249 A | 6/2000 | Cunningham et al. |
| 6,071,251 A | 6/2000 | Cunningham et al. |
| 6,071,294 A | 6/2000 | Simons et al. |

| | | | |
|---|---|---|---|
| 6,071,391 A | 6/2000 | Gotoh et al. | |
| 6,073,031 A | 6/2000 | Helstab et al. | |
| 6,081,736 A | 6/2000 | Colvin et al. | |
| 6,083,710 A | 7/2000 | Heller et al. | |
| 6,088,608 A | 7/2000 | Schulman et al. | |
| 6,091,975 A | 7/2000 | Daddona et al. | |
| 6,091,976 A | 7/2000 | Pfeiffer et al. | |
| 6,093,156 A | 7/2000 | Cunningham et al. | |
| 6,093,167 A | 7/2000 | Houben et al. | |
| 6,093,172 A | 7/2000 | Funderburk et al. | |
| 6,097,831 A | 8/2000 | Wieck et al. | |
| 6,099,484 A | 8/2000 | Douglas et al. | |
| 6,101,478 A | 8/2000 | Brown | |
| 6,103,033 A | 8/2000 | Say et al. | |
| 6,106,780 A | 8/2000 | Douglas et al. | |
| 6,110,148 A | 8/2000 | Brown et al. | |
| 6,110,152 A | 8/2000 | Kovelman | |
| 6,113,578 A | 9/2000 | Brown | |
| 6,117,290 A | 9/2000 | Say et al. | |
| 6,119,028 A | 9/2000 | Schulman et al. | |
| 6,120,676 A | 9/2000 | Heller et al. | |
| 6,121,009 A | 9/2000 | Heller et al. | |
| 6,121,611 A | 9/2000 | Lindsay et al. | |
| 6,122,351 A | 9/2000 | Schlueter, Jr. et al. | |
| 6,125,978 A | 10/2000 | Ando et al. | |
| 6,134,461 A | 10/2000 | Say et al. | |
| 6,134,504 A | 10/2000 | Douglas et al. | |
| 6,139,718 A | 10/2000 | Kurnik et al. | |
| 6,141,573 A | 10/2000 | Kurnik et al. | |
| 6,142,939 A | 11/2000 | Eppstein et al. | |
| 6,143,164 A | 11/2000 | Heller et al. | |
| 6,144,837 A | 11/2000 | Quy | |
| 6,144,869 A | 11/2000 | Berner et al. | |
| 6,144,922 A | 11/2000 | Douglas et al. | |
| 6,148,094 A | 11/2000 | Kinsella | |
| 6,150,128 A | 11/2000 | Uretsky | |
| 6,151,586 A | 11/2000 | Brown | |
| 6,153,062 A | 11/2000 | Saito et al. | |
| 6,153,069 A | 11/2000 | Pottgen et al. | |
| 6,159,147 A | 12/2000 | Lichter et al. | |
| 6,161,095 A | 12/2000 | Brown | |
| 6,162,611 A | 12/2000 | Heller et al. | |
| 6,162,639 A | 12/2000 | Douglas | |
| 6,167,362 A | 12/2000 | Brown et al. | |
| 6,168,563 B1 | 1/2001 | Brown | |
| 6,170,318 B1 | 1/2001 | Lewis | |
| 6,175,752 B1 | 1/2001 | Say et al. | |
| 6,180,416 B1 | 1/2001 | Kurnik et al. | |
| 6,185,452 B1 | 2/2001 | Schulman et al. | |
| 6,186,145 B1 | 2/2001 | Brown | |
| 6,192,891 B1 | 2/2001 | Gravel et al. | |
| 6,193,873 B1 | 2/2001 | Ohara et al. | |
| 6,196,970 B1 | 3/2001 | Brown | |
| 6,198,957 B1 | 3/2001 | Green | |
| 6,200,265 B1 | 3/2001 | Walsh et al. | |
| 6,201,979 B1 | 3/2001 | Kurnik et al. | |
| 6,201,980 B1 | 3/2001 | Darrow et al. | |
| 6,206,841 B1 | 3/2001 | Cunningham et al. | |
| 6,207,400 B1 | 3/2001 | Kwon | |
| 6,208,894 B1 | 3/2001 | Schulman et al. | |
| 6,210,272 B1 | 4/2001 | Brown | |
| 6,210,976 B1 | 4/2001 | Sabbadini | |
| 6,212,416 B1 | 4/2001 | Ward et al. | |
| 6,219,565 B1 | 4/2001 | Cupp et al. | |
| 6,219,574 B1 | 4/2001 | Cormier et al. | |
| 6,224,745 B1 | 5/2001 | Baltruschat | |
| 6,232,130 B1 | 5/2001 | Wolf | |
| 6,232,370 B1 | 5/2001 | Kubota et al. | |
| 6,233,471 B1 | 5/2001 | Berner et al. | |
| 6,233,539 B1 | 5/2001 | Brown | |
| 6,239,925 B1 | 5/2001 | Ardrey et al. | |
| 6,241,862 B1 | 6/2001 | McAleer et al. | |
| 6,246,330 B1 | 6/2001 | Nielsen | |
| 6,246,992 B1 | 6/2001 | Brown | |
| 6,248,065 B1 | 6/2001 | Brown | |
| 6,248,067 B1 | 6/2001 | Causey, III et al. | |
| 6,248,093 B1 | 6/2001 | Moberg | |
| 6,251,260 B1 | 6/2001 | Heller et al. | |
| 6,252,032 B1 | 6/2001 | Van Antwerp et al. | |
| 6,253,804 B1 | 7/2001 | Safabash | |
| 6,254,586 B1 | 7/2001 | Mann et al. | |
| 6,256,643 B1 | 7/2001 | Cork et al. | |
| 6,259,587 B1 | 7/2001 | Sheldon et al. | |
| 6,259,937 B1 | 7/2001 | Schulman et al. | |
| 6,260,022 B1 | 7/2001 | Brown | |
| 6,266,645 B1 | 7/2001 | Simpson | |
| 6,267,724 B1 | 7/2001 | Taylor | |
| 6,268,161 B1 | 7/2001 | Han et al. | |
| 6,270,445 B1 | 8/2001 | Dean, Jr. et al. | |
| 6,272,364 B1 | 8/2001 | Kurnik | |
| 6,275,717 B1 | 8/2001 | Gross et al. | |
| 6,280,416 B1 | 8/2001 | Van Antwerp et al. | |
| 6,280,587 B1 | 8/2001 | Matsumoto | |
| 6,281,006 B1 | 8/2001 | Heller et al. | |
| 6,283,943 B1 | 9/2001 | Dy et al. | |
| 6,284,126 B1 | 9/2001 | Kurnik et al. | |
| 6,284,478 B1 | 9/2001 | Heller et al. | |
| 6,293,925 B1 | 9/2001 | Safabash et al. | |
| 6,294,281 B1 | 9/2001 | Heller | |
| 6,295,463 B1 | 9/2001 | Stenzler | |
| 6,295,506 B1 | 9/2001 | Heinonen et al. | |
| 6,298,254 B2 | 10/2001 | Tamada | |
| 6,299,578 B1 | 10/2001 | Kurnik et al. | |
| 6,299,757 B1 | 10/2001 | Feldman et al. | |
| 6,301,499 B1 | 10/2001 | Carlson et al. | |
| 6,304,766 B1 | 10/2001 | Colvin, Jr. et al. | |
| 6,306,104 B1 | 10/2001 | Cunningham et al. | |
| 6,309,351 B1 | 10/2001 | Kurnik et al. | |
| 6,309,884 B1 | 10/2001 | Cooper et al. | |
| 6,315,721 B2 | 11/2001 | Schulman et al. | |
| 6,319,540 B1 | 11/2001 | Van Antwerp et al. | |
| 6,326,160 B1 | 12/2001 | Dunn et al. | |
| 6,329,161 B1 | 12/2001 | Heller et al. | |
| 6,329,929 B1 | 12/2001 | Weijand et al. | |
| 6,330,426 B2 | 12/2001 | Brown et al. | |
| 6,330,464 B1 | 12/2001 | Colvin, Jr. et al. | |
| 6,331,518 B2 | 12/2001 | Hemm et al. | |
| 6,334,778 B1 | 1/2002 | Brown | |
| 6,336,900 B1 | 1/2002 | Alleckson et al. | |
| 6,338,790 B1 | 1/2002 | Feldman et al. | |
| 6,340,421 B1 | 1/2002 | Vachon et al. | |
| 6,341,232 B1 | 1/2002 | Conn et al. | |
| 6,356,776 B1 | 3/2002 | Berner et al. | |
| 6,360,888 B1 | 3/2002 | McIvor et al. | |
| 6,366,793 B1 | 4/2002 | Bell et al. | |
| 6,366,794 B1 | 4/2002 | Moussy et al. | |
| 6,368,141 B1 | 4/2002 | Van Antwerp et al. | |
| 6,368,274 B1 | 4/2002 | Van Antwerp et al. | |
| 6,370,410 B2 | 4/2002 | Kurnik et al. | |
| 6,377,828 B1 | 4/2002 | Chaiken et al. | |
| 6,379,301 B1 | 4/2002 | Worthington et al. | |
| 6,383,767 B1 | 5/2002 | Polak | |
| 6,387,048 B1 | 5/2002 | Schulman et al. | |
| 6,391,643 B1 | 5/2002 | Chen et al. | |
| 6,392,381 B1 | 5/2002 | Chen | |
| 6,398,562 B1 | 6/2002 | Butler et al. | |
| 6,405,066 B1 | 6/2002 | Essenpreis et al. | |
| 6,413,393 B1 | 7/2002 | Van Antwerp et al. | |
| 6,418,332 B1 | 7/2002 | Mastrototaro et al. | |
| 6,424,847 B1 | 7/2002 | Mastrototaro et al. | |
| 6,427,088 B1 | 7/2002 | Bowman, IV et al. | |
| 6,429,763 B1 * | 8/2002 | Patel et al. .................. 336/200 | |
| 6,434,409 B1 | 8/2002 | Pfeiffer et al. | |
| 6,438,414 B1 | 8/2002 | Conn et al. | |
| 6,440,068 B1 | 8/2002 | Brown et al. | |
| 6,442,637 B1 | 8/2002 | Hawkins et al. | |

| Patent | Date | Inventor |
|---|---|---|
| 6,443,942 B2 | 9/2002 | Van Antwerp et al. |
| 6,454,710 B1 | 9/2002 | Ballerstadt et al. |
| 6,462,162 B2 | 10/2002 | Van Antwerp et al. |
| 6,464,848 B1 | 10/2002 | Matsumoto |
| 6,466,810 B1 | 10/2002 | Ward et al. |
| 6,468,222 B1 | 10/2002 | Mault et al. |
| 6,472,122 B1 | 10/2002 | Schulman et al. |
| 6,475,750 B1 | 11/2002 | Han et al. |
| 6,477,395 B2 | 11/2002 | Schulman et al. |
| 6,478,736 B1 | 11/2002 | Mault |
| 6,480,730 B2 | 11/2002 | Darrow et al. |
| 6,482,158 B2 | 11/2002 | Mault |
| 6,482,604 B2 | 11/2002 | Kwon |
| 6,484,045 B1 | 11/2002 | Holker et al. |
| 6,484,046 B1 | 11/2002 | Say et al. |
| 6,485,138 B1 | 11/2002 | Kubota et al. |
| 6,494,830 B1 | 12/2002 | Wessel |
| 6,496,728 B2 | 12/2002 | Li et al. |
| 6,505,059 B1 | 1/2003 | Kollias et al. |
| 6,512,939 B1 | 1/2003 | Colvin et al. |
| 6,513,532 B2 | 2/2003 | Mault et al. |
| 6,514,718 B2 | 2/2003 | Heller et al. |
| 6,515,593 B1 | 2/2003 | Stark et al. |
| 6,520,326 B2 | 2/2003 | McIvor et al. |
| 6,529,755 B2 | 3/2003 | Kurnik et al. |
| 6,529,772 B2 | 3/2003 | Carlson et al. |
| 6,530,915 B1 | 3/2003 | Eppstein et al. |
| 6,534,322 B1 | 3/2003 | Sabbadini |
| 6,534,323 B1 | 3/2003 | Sabbadini |
| 6,535,753 B1 | 3/2003 | Raskas |
| 6,537,243 B1 | 3/2003 | Henning et al. |
| 6,540,675 B2 | 4/2003 | Aceti et al. |
| 6,544,212 B2 | 4/2003 | Galley et al. |
| 6,546,268 B1 * | 4/2003 | Ishikawa et al. ............ 600/345 |
| 6,546,269 B1 | 4/2003 | Kurnik |
| 6,549,796 B2 | 4/2003 | Sohrab |
| 6,551,276 B1 | 4/2003 | Mann et al. |
| 6,551,494 B1 | 4/2003 | Heller et al. |
| 6,553,244 B2 | 4/2003 | Lesho et al. |
| 6,554,798 B1 | 4/2003 | Mann et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,571,200 B1 | 5/2003 | Mault |
| 6,576,101 B1 | 6/2003 | Heller et al. |
| 6,576,117 B1 | 6/2003 | Iketaki et al. |
| 6,577,899 B2 | 6/2003 | Lebel et al. |
| 6,579,498 B1 | 6/2003 | Eglise |
| 6,579,690 B1 | 6/2003 | Bonnecaze et al. |
| 6,584,335 B1 | 6/2003 | Haar et al. |
| 6,585,644 B2 | 7/2003 | Lebel et al. |
| 6,587,705 B1 | 7/2003 | Kim et al. |
| 6,591,125 B1 | 7/2003 | Buse et al. |
| 6,591,126 B2 | 7/2003 | Roeper et al. |
| 6,594,514 B2 | 7/2003 | Berner et al. |
| 6,595,919 B2 | 7/2003 | Berner et al. |
| 6,595,929 B2 | 7/2003 | Stivoric et al. |
| 6,602,678 B2 | 8/2003 | Kwon et al. |
| 6,602,909 B2 | 8/2003 | Jarowski |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,612,306 B1 | 9/2003 | Mault |
| 6,615,078 B1 | 9/2003 | Burson et al. |
| 6,618,603 B2 | 9/2003 | Varalli et al. |
| 6,620,106 B2 | 9/2003 | Mault |
| 6,627,058 B1 | 9/2003 | Chan |
| 6,629,934 B2 | 10/2003 | Mault et al. |
| 6,633,772 B2 | 10/2003 | Ford et al. |
| 6,635,014 B2 | 10/2003 | Starkweather et al. |
| 6,641,533 B2 | 11/2003 | Causey, III et al. |
| 6,642,015 B2 | 11/2003 | Vachon et al. |
| 6,645,142 B2 | 11/2003 | Braig et al. |
| 6,648,821 B2 | 11/2003 | Lebel et al. |
| 6,653,091 B1 | 11/2003 | Dunn et al. |
| 6,654,625 B1 | 11/2003 | Say et al. |
| 6,659,948 B2 | 12/2003 | Lebel et al. |
| 6,668,196 B1 | 12/2003 | Villegas et al. |
| 6,671,554 B2 | 12/2003 | Gibson et al. |
| 6,673,625 B2 | 1/2004 | Satcher, Jr. et al. |
| 6,682,938 B1 | 1/2004 | Satcher, Jr. et al. |
| 6,683,040 B2 | 1/2004 | Bragulla et al. |
| 6,687,522 B2 | 2/2004 | Tamada |
| 6,687,546 B2 | 2/2004 | Lebel et al. |
| 6,689,056 B1 | 2/2004 | Kilcoyne et al. |
| 6,693,069 B2 | 2/2004 | Korber et al. |
| 6,694,158 B2 | 2/2004 | Polak |
| 6,694,191 B2 | 2/2004 | Starkweather et al. |
| 6,695,860 B1 | 2/2004 | Ward et al. |
| 6,702,857 B2 | 3/2004 | Brauker et al. |
| 6,704,587 B1 | 3/2004 | Kumar et al. |
| 6,711,423 B2 | 3/2004 | Colvin, Jr. |
| 6,723,046 B2 | 4/2004 | Lichtenstein et al. |
| 6,728,560 B2 | 4/2004 | Kollias et al. |
| 6,731,976 B2 | 5/2004 | Penn et al. |
| 6,733,446 B2 | 5/2004 | Lebel et al. |
| 6,734,162 B2 | 5/2004 | Van Antwerp et al. |
| 6,736,777 B2 | 5/2004 | Kim et al. |
| 6,737,401 B2 | 5/2004 | Kim et al. |
| 6,738,654 B2 | 5/2004 | Sohrab |
| 6,740,075 B2 | 5/2004 | Lebel et al. |
| 6,741,163 B1 | 5/2004 | Roberts |
| 6,741,876 B1 | 5/2004 | Scecina et al. |
| 6,741,877 B1 | 5/2004 | Shults et al. |
| 6,746,582 B2 | 6/2004 | Heller et al. |
| 6,749,587 B2 | 6/2004 | Flaherty |
| 6,750,311 B1 | 6/2004 | Van Antwerp et al. |
| 6,758,810 B2 | 7/2004 | Lebel et al. |
| 6,766,183 B2 | 7/2004 | Walsh et al. |
| 6,766,201 B2 | 7/2004 | Von Arx et al. |
| 6,768,425 B2 | 7/2004 | Flaherty et al. |
| 6,770,030 B1 | 8/2004 | Schaupp et al. |
| 6,770,729 B2 | 8/2004 | Van Antwerp et al. |
| 6,771,995 B2 | 8/2004 | Kurnik et al. |
| 6,773,563 B2 | 8/2004 | Matsumoto |
| 6,780,297 B2 | 8/2004 | Matsumoto et al. |
| 6,780,871 B2 | 8/2004 | Glick et al. |
| 6,784,274 B2 | 8/2004 | Van Antwerp et al. |
| 6,790,178 B1 | 9/2004 | Mault et al. |
| 6,794,195 B2 | 9/2004 | Colvin, Jr. |
| 6,800,451 B2 | 10/2004 | Daniloff et al. |
| 6,804,544 B2 | 10/2004 | Van Antwerp et al. |
| 6,809,507 B2 | 10/2004 | Morgan et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,811,659 B2 | 11/2004 | Vachon |
| 6,812,031 B1 | 11/2004 | Carlsson |
| 6,813,519 B2 | 11/2004 | Lebel et al. |
| 6,816,742 B2 | 11/2004 | Kim et al. |
| 6,835,553 B2 | 12/2004 | Han et al. |
| RE38,681 E | 1/2005 | Kurnik et al. |
| 6,840,912 B2 | 1/2005 | Kloepfer et al. |
| 6,844,023 B2 | 1/2005 | Schulman et al. |
| 6,849,237 B2 | 2/2005 | Housefield et al. |
| 6,850,790 B2 | 2/2005 | Berner et al. |
| 6,852,500 B1 | 2/2005 | Hoss et al. |
| 6,852,694 B2 | 2/2005 | Van Antwerp et al. |

| | | |
|---|---|---|
| 6,853,854 B1 | 2/2005 | Proniewicz et al. |
| 6,856,928 B2 | 2/2005 | Harmon |
| 6,858,403 B2 | 2/2005 | Han et al. |
| 6,862,465 B2 | 3/2005 | Shults et al. |
| 6,862,466 B2 | 3/2005 | Ackerman |
| 6,872,200 B2 | 3/2005 | Mann et al. |
| 6,873,268 B2 | 3/2005 | Lebel et al. |
| 6,881,551 B2 | 4/2005 | Heller et al. |
| 6,882,940 B2 | 4/2005 | Potts et al. |
| 6,885,883 B2 | 4/2005 | Parris et al. |
| 6,892,085 B2 | 5/2005 | McIvor et al. |
| 6,895,263 B2 | 5/2005 | Shin et al. |
| 6,895,265 B2 | 5/2005 | Silver |
| 6,899,683 B2 | 5/2005 | Mault et al. |
| 6,899,684 B2 | 5/2005 | Mault et al. |
| 6,902,905 B2 | 6/2005 | Burson et al. |
| 6,904,301 B2 | 6/2005 | Raskas |
| 6,907,127 B1 | 6/2005 | Kravitz et al. |
| 6,915,147 B2 | 7/2005 | Lebel et al. |
| 6,918,874 B1 | 7/2005 | Hatch et al. |
| 6,922,578 B2 | 7/2005 | Eppstein et al. |
| RE38,775 E | 8/2005 | Kurnik et al. |
| 6,923,764 B2 | 8/2005 | Aceti et al. |
| 6,923,936 B2 | 8/2005 | Swanson et al. |
| 6,927,246 B2 | 8/2005 | Noronha et al. |
| 6,931,327 B2 | 8/2005 | Goode, Jr. et al. |
| 6,936,006 B2 | 8/2005 | Sabra |
| 6,936,029 B2 | 8/2005 | Mann et al. |
| 6,940,590 B2 | 9/2005 | Colvin, Jr. et al. |
| 6,941,163 B2 | 9/2005 | Ford et al. |
| 6,950,708 B2 | 9/2005 | Bowman, IV et al. |
| 6,952,603 B2 | 10/2005 | Gerber et al. |
| 6,954,673 B2 | 10/2005 | Von Arx et al. |
| 6,955,650 B2 | 10/2005 | Mault et al. |
| 6,957,102 B2 | 10/2005 | Silver et al. |
| 6,957,107 B2 | 10/2005 | Rogers et al. |
| 6,958,705 B2 | 10/2005 | Lebel et al. |
| 6,968,294 B2 | 11/2005 | Gutta et al. |
| 6,968,375 B1 | 11/2005 | Brown |
| 6,971,274 B2 | 12/2005 | Olin |
| 6,974,437 B2 | 12/2005 | Lebel et al. |
| 6,978,182 B2 | 12/2005 | Mazar et al. |
| 6,979,326 B2 | 12/2005 | Mann et al. |
| 6,990,366 B2 | 1/2006 | Say et al. |
| 6,991,096 B2 | 1/2006 | Gottlieb et al. |
| 6,997,907 B2 | 2/2006 | Safabash et al. |
| 6,997,920 B2 | 2/2006 | Mann et al. |
| 6,998,247 B2 | 2/2006 | Monfre et al. |
| 6,999,810 B2 | 2/2006 | Berner et al. |
| 7,003,336 B2 | 2/2006 | Holker et al. |
| 7,003,340 B2 | 2/2006 | Say et al. |
| 7,003,341 B2 | 2/2006 | Say et al. |
| 7,004,901 B2 | 2/2006 | Fish |
| 7,005,857 B2 | 2/2006 | Stiene et al. |
| 7,011,630 B2 | 3/2006 | Desai et al. |
| 7,018,366 B2 | 3/2006 | Easter |
| 7,018,568 B2 | 3/2006 | Tierney |
| 7,022,072 B2 | 4/2006 | Fox et al. |
| 7,024,236 B2 | 4/2006 | Ford et al. |
| 7,024,245 B2 | 4/2006 | Lebel et al. |
| 7,025,743 B2 | 4/2006 | Mann et al. |
| 7,029,444 B2 | 4/2006 | Shin et al. |
| 7,039,810 B1 | 5/2006 | Nichols |
| 7,041,068 B2 | 5/2006 | Freeman et al. |
| 7,041,468 B2 | 5/2006 | Drucker et al. |
| 7,049,277 B2 | 5/2006 | Bagulla et al. |
| 7,052,472 B1 | 5/2006 | Miller et al. |
| 7,052,483 B2 | 5/2006 | Wojcik |
| 7,056,302 B2 | 6/2006 | Douglas |
| 7,074,307 B2 | 7/2006 | Simpson et al. |
| 7,081,195 B2 | 7/2006 | Simpson et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,133,710 B2 | 11/2006 | Acosta et al. |
| 7,134,999 B2 | 11/2006 | Brauker et al. |
| 7,136,689 B2 | 11/2006 | Shults et al. |
| 7,150,975 B2 | 12/2006 | Tamada et al. |
| 7,163,511 B2 | 1/2007 | Conn et al. |
| 7,171,274 B2 | 1/2007 | Starkweather et al. |
| 7,183,068 B2 | 2/2007 | Burson et al. |
| 7,183,102 B2 | 2/2007 | Monfre et al. |
| 7,189,341 B2 | 3/2007 | Li et al. |
| 7,190,988 B2 | 3/2007 | Say et al. |
| 7,191,013 B1 * | 3/2007 | Miranda et al. ............... 607/60 |
| 7,192,450 B2 | 3/2007 | Brauker et al. |
| 7,198,606 B2 | 4/2007 | Boecker et al. |
| 7,226,978 B2 | 6/2007 | Tapsak et al. |
| 7,228,163 B2 | 6/2007 | Ackerman |
| 7,233,817 B2 | 6/2007 | Yen |
| 7,261,691 B1 | 8/2007 | Asomani |
| 7,276,029 B2 | 10/2007 | Goode, Jr. et al. |
| 7,295,867 B2 | 11/2007 | Berner et al. |
| 7,310,544 B2 | 12/2007 | Brister et al. |
| 2001/0011224 A1 | 8/2001 | Brown |
| 2001/0016310 A1 | 8/2001 | Brown et al. |
| 2001/0016682 A1 | 8/2001 | Berner et al. |
| 2001/0016683 A1 | 8/2001 | Darrow et al. |
| 2001/0020124 A1 | 9/2001 | Tamada |
| 2001/0029340 A1 | 10/2001 | Mault et al. |
| 2001/0032278 A1 | 10/2001 | Brown et al. |
| 2001/0037060 A1 | 11/2001 | Thompson et al. |
| 2001/0037069 A1 | 11/2001 | Carlson et al. |
| 2001/0039504 A1 | 11/2001 | Linberg et al. |
| 2001/0041830 A1 | 11/2001 | Varalli et al. |
| 2001/0041831 A1 | 11/2001 | Starkweather et al. |
| 2001/0044581 A1 | 11/2001 | Mault |
| 2001/0044588 A1 | 11/2001 | Mault |
| 2001/0047125 A1 | 11/2001 | Quy |
| 2001/0049096 A1 | 12/2001 | Brown |
| 2001/0049470 A1 | 12/2001 | Mault et al. |
| 2002/0002326 A1 | 1/2002 | Causey, III et al. |
| 2002/0002328 A1 | 1/2002 | Tamada |
| 2002/0004640 A1 | 1/2002 | Conn et al. |
| 2002/0010414 A1 | 1/2002 | Coston et al. |
| 2002/0016530 A1 | 2/2002 | Brown |
| 2002/0019022 A1 | 2/2002 | Dunn et al. |
| 2002/0019586 A1 | 2/2002 | Teller et al. |
| 2002/0019748 A1 | 2/2002 | Brown |
| 2002/0026937 A1 | 3/2002 | Mault |
| 2002/0027164 A1 | 3/2002 | Mault et al. |
| 2002/0028995 A1 | 3/2002 | Mault |
| 2002/0040208 A1 | 4/2002 | Flaherty et al. |
| 2002/0042090 A1 | 4/2002 | Heller et al. |
| 2002/0047867 A1 | 4/2002 | Mault et al. |
| 2002/0053637 A1 | 5/2002 | Conn et al. |
| 2002/0062069 A1 | 5/2002 | Mault |
| 2002/0063060 A1 | 5/2002 | Gascoyne et al. |
| 2002/0068858 A1 | 6/2002 | Braig et al. |
| 2002/0072858 A1 | 6/2002 | Cheng |
| 2002/0077765 A1 | 6/2002 | Mault |
| 2002/0077766 A1 | 6/2002 | Mault |
| 2002/0081559 A1 | 6/2002 | Brown et al. |
| 2002/0083461 A1 | 6/2002 | Hutcheson et al. |
| 2002/0087056 A1 | 7/2002 | Aceti et al. |
| 2002/0091312 A1 | 7/2002 | Berner et al. |
| 2002/0103425 A1 | 8/2002 | Mault |
| 2002/0103499 A1 | 8/2002 | Perez et al. |
| 2002/0106709 A1 | 8/2002 | Potts et al. |
| 2002/0107433 A1 | 8/2002 | Mault |
| 2002/0107476 A1 | 8/2002 | Mann et al. |
| 2002/0109600 A1 | 8/2002 | Mault et al. |
| 2002/0119711 A1 | 8/2002 | Van Antwerp et al. |
| 2002/0124017 A1 | 9/2002 | Mault |
| 2002/0128594 A1 | 9/2002 | Das et al. |

| | | | | | | |
|---|---|---|---|---|---|---|
| 2002/0130042 A1 | 9/2002 | Moerman et al. | | 2004/0073095 A1 | 4/2004 | Causey, III et al. |
| 2002/0133378 A1 | 9/2002 | Mault et al. | | 2004/0096959 A1 | 5/2004 | Stiene et al. |
| 2002/0161286 A1 | 10/2002 | Gerber et al. | | 2004/0106858 A1 | 6/2004 | Say et al. |
| 2002/0161288 A1 | 10/2002 | Shin et al. | | 2004/0108226 A1 | 6/2004 | Polychronakos et al. |
| 2002/0177764 A1 | 11/2002 | Sohrab | | 2004/0122353 A1 | 6/2004 | Shahmirian et al. |
| 2002/0193679 A1 | 12/2002 | Malave et al. | | 2004/0122489 A1 | 6/2004 | Mazar et al. |
| 2003/0023182 A1 | 1/2003 | Mault et al. | | 2004/0133164 A1 | 7/2004 | Funderburk et al. |
| 2003/0023317 A1 | 1/2003 | Brauker et al. | | 2004/0138588 A1 | 7/2004 | Saikley et al. |
| 2003/0028089 A1 | 2/2003 | Galley et al. | | 2004/0152622 A1 | 8/2004 | Keith et al. |
| 2003/0028120 A1 | 2/2003 | Mault et al. | | 2004/0153585 A1 | 8/2004 | Kawatahara et al. |
| 2003/0032077 A1 | 2/2003 | Itoh et al. | | 2004/0162473 A1 | 8/2004 | Sohrab |
| 2003/0032867 A1 | 2/2003 | Crothall et al. | | 2004/0164961 A1 | 8/2004 | Bal et al. |
| 2003/0032868 A1 | 2/2003 | Graskov et al. | | 2004/0167383 A1 | 8/2004 | Kim et al. |
| 2003/0032874 A1 | 2/2003 | Rhodes et al. | | 2004/0167801 A1 | 8/2004 | Say et al. |
| 2003/0040683 A1 | 2/2003 | Rule et al. | | 2004/0171921 A1 | 9/2004 | Say et al. |
| 2003/0042137 A1 | 3/2003 | Mao et al. | | 2004/0172284 A1 | 9/2004 | Sullivan et al. |
| 2003/0050537 A1 | 3/2003 | Wessel | | 2004/0176672 A1 | 9/2004 | Silver et al. |
| 2003/0050546 A1 | 3/2003 | Desai et al. | | 2004/0176913 A1 | 9/2004 | Kawatahara et al. |
| 2003/0065257 A1 | 4/2003 | Mault et al. | | 2004/0186362 A1 | 9/2004 | Brauker et al. |
| 2003/0065273 A1 | 4/2003 | Mault et al. | | 2004/0186365 A1 | 9/2004 | Jin et al. |
| 2003/0065274 A1 | 4/2003 | Mault et al. | | 2004/0193025 A1 | 9/2004 | Steil et al. |
| 2003/0065275 A1 | 4/2003 | Mault et al. | | 2004/0193090 A1 | 9/2004 | Lebel et al. |
| 2003/0065308 A1 | 4/2003 | Lebel et al. | | 2004/0199059 A1 | 10/2004 | Brauker et al. |
| 2003/0100040 A1 | 5/2003 | Bonnecaze et al. | | 2004/0202576 A1 | 10/2004 | Aceti et al. |
| 2003/0100821 A1 | 5/2003 | Heller et al. | | 2004/0204687 A1 | 10/2004 | Mogensen et al. |
| 2003/0105407 A1 | 6/2003 | Pearce et al. | | 2004/0208780 A1 | 10/2004 | Faries, Jr. et al. |
| 2003/0108976 A1 | 6/2003 | Braig et al. | | 2004/0225338 A1 | 11/2004 | Lebel et al. |
| 2003/0130616 A1 | 7/2003 | Steil et al. | | 2004/0248204 A1 | 12/2004 | Moerman |
| 2003/0134347 A1 | 7/2003 | Heller et al. | | 2004/0249250 A1 | 12/2004 | McGee et al. |
| 2003/0135100 A1 | 7/2003 | Kim et al. | | 2004/0249253 A1 | 12/2004 | Racchini et al. |
| 2003/0135333 A1 | 7/2003 | Aceti et al. | | 2004/0249254 A1 | 12/2004 | Racchini et al. |
| 2003/0153820 A1 | 8/2003 | Berner et al. | | 2004/0249999 A1 | 12/2004 | Connolly et al. |
| 2003/0153821 A1 | 8/2003 | Berner et al. | | 2004/0253736 A1 | 12/2004 | Stout et al. |
| 2003/0158472 A1 | 8/2003 | Sohrab | | 2004/0254429 A1 | 12/2004 | Yang |
| 2003/0158707 A1 | 8/2003 | Doi | | 2004/0254433 A1 | 12/2004 | Bandis et al. |
| 2003/0168338 A1 | 9/2003 | Gao et al. | | 2004/0254434 A1 | 12/2004 | Goodnow et al. |
| 2003/0175806 A1 | 9/2003 | Rule et al. | | 2004/0260363 A1 | 12/2004 | Von Arx et al. |
| 2003/0176183 A1 | 9/2003 | Drucker et al. | | 2004/0263354 A1 | 12/2004 | Mann et al. |
| 2003/0176933 A1 | 9/2003 | Lebel et al. | | 2004/0267300 A1 | 12/2004 | Mace |
| 2003/0181851 A1 | 9/2003 | Mann et al. | | 2005/0003470 A1 | 1/2005 | Nelson et al. |
| 2003/0181852 A1 | 9/2003 | Mann et al. | | 2005/0004494 A1 | 1/2005 | Perez et al. |
| 2003/0187338 A1 | 10/2003 | Say et al. | | 2005/0010087 A1 | 1/2005 | Banet et al. |
| 2003/0187525 A1 | 10/2003 | Mann et al. | | 2005/0010269 A1 | 1/2005 | Lebel et al. |
| 2003/0191376 A1 | 10/2003 | Samuels et al. | | 2005/0016276 A1 | 1/2005 | Guan et al. |
| 2003/0191431 A1 | 10/2003 | Mann et al. | | 2005/0027177 A1 | 2/2005 | Shin et al. |
| 2003/0195403 A1 | 10/2003 | Berner et al. | | 2005/0027179 A1 | 2/2005 | Berner et al. |
| 2003/0195462 A1 | 10/2003 | Mann et al. | | 2005/0027180 A1 | 2/2005 | Goode, Jr. et al. |
| 2003/0199790 A1 | 10/2003 | Boecker et al. | | 2005/0027181 A1 | 2/2005 | Goode, Jr. et al. |
| 2003/0199791 A1 | 10/2003 | Boecker et al. | | 2005/0027462 A1 | 2/2005 | Goode, Jr. et al. |
| 2003/0199903 A1 | 10/2003 | Boecker et al. | | 2005/0027463 A1 | 2/2005 | Goode, Jr. et al. |
| 2003/0208110 A1 | 11/2003 | Mault et al. | | 2005/0031689 A1 | 2/2005 | Shults et al. |
| 2003/0208113 A1 | 11/2003 | Mault et al. | | 2005/0033132 A1 | 2/2005 | Shults et al. |
| 2003/0208133 A1 | 11/2003 | Mault | | 2005/0038680 A1 | 2/2005 | McMahon |
| 2003/0208409 A1 | 11/2003 | Mault | | 2005/0043598 A1 | 2/2005 | Goode, Jr. et al. |
| 2003/0212364 A1 | 11/2003 | Mann et al. | | 2005/0043894 A1 | 2/2005 | Fernandez |
| 2003/0212379 A1 | 11/2003 | Bylund et al. | | 2005/0049473 A1 | 3/2005 | Desai et al. |
| 2003/0217966 A1 | 11/2003 | Tapsak et al. | | 2005/0054909 A1 | 3/2005 | Petisce et al. |
| 2003/0226695 A1 | 12/2003 | Mault | | 2005/0090607 A1 | 4/2005 | Tapsak et al. |
| 2003/0229514 A2 | 12/2003 | Brown | | 2005/0112169 A1 | 5/2005 | Brauker et al. |
| 2003/0232370 A1 | 12/2003 | Trifiro | | 2005/0113657 A1 | 5/2005 | Alarcon et al. |
| 2003/0235817 A1 | 12/2003 | Bartkowiak et al. | | 2005/0113658 A1 | 5/2005 | Jacobson et al. |
| 2004/0010207 A1 | 1/2004 | Flaherty et al. | | 2005/0114068 A1 | 5/2005 | Chey et al. |
| 2004/0011671 A1 | 1/2004 | Shults et al. | | 2005/0118726 A1 | 6/2005 | Schultz et al. |
| 2004/0018486 A1 | 1/2004 | Dunn et al. | | 2005/0121322 A1 | 6/2005 | Say et al. |
| 2004/0039256 A1 | 2/2004 | Kawatahara et al. | | 2005/0124873 A1 | 6/2005 | Shults et al. |
| 2004/0039298 A1 | 2/2004 | Abreu | | 2005/0131346 A1 | 6/2005 | Douglas |
| 2004/0040840 A1 | 3/2004 | Mao et al. | | 2005/0137471 A1 | 6/2005 | Haar et al. |
| 2004/0045879 A1 | 3/2004 | Shults et al. | | 2005/0143635 A1 | 6/2005 | Kamath et al. |
| 2004/0054263 A1 | 3/2004 | Moerman et al. | | 2005/0143636 A1 | 6/2005 | Zhang et al. |
| 2004/0059201 A1 | 3/2004 | Ginsberg | | 2005/0148003 A1 | 7/2005 | Keith et al. |
| 2004/0064068 A1 | 4/2004 | DeNuzzio et al. | | 2005/0154271 A1 | 7/2005 | Rasdal et al. |
| 2004/0069164 A1 | 4/2004 | Nakamura et al. | | 2005/0161346 A1 | 7/2005 | Simpson et al. |
| 2004/0072357 A1 | 4/2004 | Stiene et al. | | 2005/0171503 A1 | 8/2005 | Van Den Berghe et al. |

| | | |
|---|---|---|
| 2005/0171513 A1 | 8/2005 | Mann et al. |
| 2005/0173245 A1 | 8/2005 | Feldman et al. |
| 2005/0176136 A1 | 8/2005 | Burd et al. |
| 2005/0177036 A1 | 8/2005 | Shults et al. |
| 2005/0181012 A1 | 8/2005 | Saint et al. |
| 2005/0182306 A1 | 8/2005 | Sloan |
| 2005/0182451 A1 | 8/2005 | Griffin et al. |
| 2005/0187720 A1 | 8/2005 | Goode, Jr. et al. |
| 2005/0192557 A1 | 9/2005 | Brauker et al. |
| 2005/0195930 A1 | 9/2005 | Spital et al. |
| 2005/0199494 A1 | 9/2005 | Say et al. |
| 2005/0203360 A1 | 9/2005 | Brauker et al. |
| 2005/0203707 A1 | 9/2005 | Tsutsui et al. |
| 2005/0214892 A1 | 9/2005 | Kovatchev et al. |
| 2005/0215871 A1 | 9/2005 | Feldman et al. |
| 2005/0215872 A1 | 9/2005 | Berner et al. |
| 2005/0225188 A1 | 10/2005 | Griepentrog et al. |
| 2005/0239154 A1 | 10/2005 | Feldman et al. |
| 2005/0239156 A1 | 10/2005 | Drucker et al. |
| 2005/0245795 A1 | 11/2005 | Goode, Jr. et al. |
| 2005/0245799 A1 | 11/2005 | Brauker et al. |
| 2005/0251083 A1 | 11/2005 | Carr-Brendel et al. |
| 2005/0261660 A1 | 11/2005 | Choi |
| 2005/0267780 A1 | 12/2005 | Ray et al. |
| 2005/0271546 A1 | 12/2005 | Gerber et al. |
| 2005/0271547 A1 | 12/2005 | Gerber et al. |
| 2005/0272640 A1 | 12/2005 | Doyle, III et al. |
| 2005/0272985 A1 | 12/2005 | Kotulla et al. |
| 2005/0277164 A1 | 12/2005 | Drucker et al. |
| 2005/0287620 A1 | 12/2005 | Heller et al. |
| 2006/0001538 A1 | 1/2006 | Kraft et al. |
| 2006/0001550 A1 | 1/2006 | Mann et al. |
| 2006/0001551 A1 | 1/2006 | Kraft et al. |
| 2006/0003398 A1 | 1/2006 | Heller et al. |
| 2006/0004271 A1 | 1/2006 | Peyser et al. |
| 2006/0007017 A1 | 1/2006 | Mann et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0025663 A1 | 2/2006 | Talbot et al. |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0036187 A1 | 2/2006 | Vos et al. |
| 2006/0040402 A1 | 2/2006 | Brauker et al. |
| 2006/0052679 A1 | 3/2006 | Kotulla et al. |
| 2006/0058602 A1 | 3/2006 | Kwiatkowski et al. |
| 2006/0063218 A1 | 3/2006 | Bartkowiak et al. |
| 2006/0074564 A1 | 4/2006 | Bartkowiak et al. |
| 2006/0173444 A1 | 8/2006 | Choy et al. |
| 2006/0189863 A1 | 8/2006 | Peyser et al. |
| 2006/0195029 A1 | 8/2006 | Shults et al. |
| 2006/0222566 A1 | 10/2006 | Brauker et al. |
| 2006/0226985 A1 | 10/2006 | Goodnow et al. |
| 2006/0247508 A1 | 11/2006 | Fennell |
| 2006/0247985 A1 | 11/2006 | Liamos et al. |
| 2007/0027381 A1 | 2/2007 | Stafford |
| 2007/0060814 A1 | 3/2007 | Stafford |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078323 A1 | 4/2007 | Reggiardo et al. |
| 2007/0106135 A1 | 5/2007 | Sloan et al. |
| 2007/0149873 A1 | 6/2007 | Say et al. |
| 2007/0149874 A1 | 6/2007 | Say et al. |
| 2007/0151869 A1 | 7/2007 | Heller et al. |
| 2007/0161879 A1 | 7/2007 | Say et al. |
| 2007/0161880 A1 | 7/2007 | Say et al. |
| 2007/0163880 A1 | 7/2007 | Woo et al. |
| 2007/0173706 A1 | 7/2007 | Neinast et al. |
| 2007/0179370 A1 | 8/2007 | Say et al. |
| 2007/0179372 A1 | 8/2007 | Say et al. |
| 2007/0191699 A1 | 8/2007 | Say et al. |
| 2007/0191700 A1 | 8/2007 | Say et al. |
| 2007/0203408 A1 | 8/2007 | Say et al. |
| 2007/0203410 A1 | 8/2007 | Say et al. |
| 2007/0203411 A1 | 8/2007 | Say et al. |
| 2007/0203966 A1 | 8/2007 | Brauker et al. |
| 2007/0208247 A1 | 9/2007 | Say et al. |
| 2007/0213610 A1 | 9/2007 | Say et al. |
| 2007/0215491 A1 | 9/2007 | Heller et al. |
| 2007/0218097 A1 | 9/2007 | Heller et al. |
| 2007/0235331 A1 | 10/2007 | Simpson et al. |
| 2007/0244380 A1 | 10/2007 | Say et al. |
| 2007/0249919 A1 | 10/2007 | Say et al. |
| 2007/0249920 A1 | 10/2007 | Say et al. |
| 2007/0249922 A1 | 10/2007 | Peyser et al. |
| 2008/0009692 A1 | 1/2008 | Stafford |
| 2008/0021666 A1 | 1/2008 | Goode, Jr. et al. |
| 2008/0033254 A1 | 2/2008 | Kamath et al. |
| 2008/0039702 A1 | 2/2008 | Hayter et al. |
| 2008/0045824 A1 | 2/2008 | Tapsak et al. |
| 2008/0071156 A1 | 3/2008 | Brister et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0108942 A1 | 5/2008 | Brister et al. |

FOREIGN PATENT DOCUMENTS

| | | |
|---|---|---|
| EP | 0010375 | 4/1980 |
| EP | 1579690 | 11/1980 |
| EP | 0026995 | 4/1981 |
| EP | 0048090 | 3/1982 |
| EP | 0078636 | 5/1983 |
| EP | 0080304 | 6/1983 |
| EP | 0098592 | 1/1984 |
| EP | 0125139 | 11/1984 |
| EP | 0127958 | 12/1984 |
| EP | 0136362 | 4/1985 |
| EP | 0170375 | 2/1986 |
| EP | 0177743 | 4/1986 |
| EP | 0184909 | 6/1986 |
| EP | 0206218 | 12/1986 |
| EP | 0230472 | 8/1987 |
| EP | 0241309 | 10/1987 |
| EP | 0245073 | 11/1987 |
| EP | 0255291 | 2/1988 |
| EP | 0278647 | 8/1988 |
| EP | 0320109 | 6/1989 |
| EP | 0353328 | 2/1990 |
| EP | 0359831 | 3/1990 |
| EP | 0368209 | 5/1990 |
| EP | 0368290 | 5/1990 |
| EP | 0390390 | 10/1990 |
| EP | 0396788 | 11/1990 |
| EP | 0400918 | 12/1990 |
| EP | 0453283 | 10/1991 |
| EP | 0470290 | 2/1992 |
| EP | 0504835 | 9/1992 |
| EP | 0286118 | 1/1995 |

| | | |
|---|---|---|
| EP | 0653718 | 5/1995 |
| EP | 0800082 | 10/1997 |
| EP | 0880936 | 12/1998 |
| EP | 0970655 | 1/2000 |
| EP | 1034734 | 9/2000 |
| EP | 1048264 | 11/2000 |
| EP | 1445746 | 8/2004 |
| GB | 1394171 | 5/1975 |
| GB | 1579690 | 11/1980 |
| GB | 1599241 | 9/1981 |
| GB | 2073891 | 10/1981 |
| GB | 2154003 | 8/1985 |
| GB | 2194892 | 3/1988 |
| GB | 2204408 | 11/1988 |
| GB | 2225637 | 6/1990 |
| GB | 2254436 | 10/1992 |
| JP | 54-041191 | 4/1979 |
| JP | 55-012406 | 1/1980 |
| JP | 56-163447 | 12/1981 |
| JP | 57-070448 | 4/1982 |
| JP | 60-173457 | 9/1985 |
| JP | 60-173458 | 9/1985 |
| JP | 60-173459 | 9/1985 |
| JP | 61-090050 | 5/1986 |
| JP | 62-085855 | 4/1987 |
| JP | 62-114747 | 5/1987 |
| JP | 63-058149 | 3/1988 |
| JP | 63-128252 | 5/1988 |
| JP | 63-139246 | 6/1988 |
| JP | 63-294799 | 12/1988 |
| JP | 63-317757 | 12/1988 |
| JP | 63-317758 | 12/1988 |
| JP | 1-114746 | 5/1989 |
| JP | 1-114747 | 5/1989 |
| JP | 1-134244 | 5/1989 |
| JP | 1-156658 | 6/1989 |
| JP | 2-062958 | 3/1990 |
| JP | 2-120655 | 5/1990 |
| JP | 2-287145 | 11/1990 |
| JP | 2-310457 | 12/1990 |
| JP | 3-026956 | 2/1991 |
| JP | 3-028752 | 2/1991 |
| JP | 3-202764 | 9/1991 |
| JP | 5-072171 | 3/1993 |
| JP | 5-196595 | 8/1993 |
| JP | 6-190050 | 7/1994 |
| JP | 7-055757 | 3/1995 |
| JP | 7-072585 | 3/1995 |
| JP | 8-154903 | 6/1996 |
| JP | 8-285814 | 11/1996 |
| JP | 8-285815 | 11/1996 |
| JP | 9-021778 | 1/1997 |
| JP | 9-101280 | 4/1997 |
| JP | 9-285459 | 11/1997 |
| JP | 10-170471 | 6/1998 |
| JP | 2000-000231 | 1/2000 |
| JP | 2000-116628 | 4/2000 |
| WO | WO-85/05119 | 11/1985 |
| WO | WO-86/00513 | 1/1986 |
| WO | WO-87/00513 | 1/1987 |
| WO | WO-87/06040 | 10/1987 |
| WO | WO-89/02246 | 3/1989 |
| WO | WO-89/05119 | 6/1989 |
| WO | WO-89/08713 | 9/1989 |
| WO | WO-90/00367 | 1/1990 |
| WO | WO-90/05300 | 5/1990 |
| WO | WO-90/05910 | 5/1990 |
| WO | WO-91/01680 | 2/1991 |
| WO | WO-91/04704 | 4/1991 |
| WO | WO-91/15993 | 10/1991 |
| WO | WO-92/13271 | 8/1992 |
| WO | WO-94/20602 | 9/1994 |
| WO | WO-94/27140 | 11/1994 |
| WO | WO-95/06240 | 3/1995 |
| WO | WO-96/07908 | 3/1996 |
| WO | WO-96/25089 | 8/1996 |
| WO | WO-96/30431 | 10/1996 |
| WO | WO-96/35370 | 11/1996 |
| WO | WO-97/02847 | 1/1997 |
| WO | WO-97/19344 | 5/1997 |
| WO | WO-97/20207 | 6/1997 |
| WO | WO-97/41421 | 11/1997 |
| WO | WO-97/42882 | 11/1997 |
| WO | WO-97/42883 | 11/1997 |
| WO | WO-97/42886 | 11/1997 |
| WO | WO-97/42888 | 11/1997 |
| WO | WO-97/43962 | 11/1997 |
| WO | WO-97/46868 | 12/1997 |
| WO | WO-98/09167 | 3/1998 |
| WO | WO-98/24366 | 6/1998 |
| WO | WO-98/35053 | 8/1998 |
| WO | WO-98/52045 | 11/1998 |
| WO | WO-98/52293 | 11/1998 |
| WO | WO-99/05966 | 2/1999 |
| WO | WO-99/32883 | 7/1999 |
| WO | WO-99/56613 | 11/1999 |
| WO | WO-00/13580 | 3/2000 |
| WO | WO-00/18294 | 4/2000 |
| WO | WO-00/19887 | 4/2000 |
| WO | WO-00/20626 | 4/2000 |
| WO | WO-00/33065 | 6/2000 |
| WO | WO-00/49940 | 8/2000 |
| WO | WO-00/59370 | 10/2000 |
| WO | WO-00/62664 | 10/2000 |
| WO | WO-00/62665 | 10/2000 |
| WO | WO-00/78210 | 12/2000 |
| WO | WO-00/78992 | 12/2000 |
| WO | WO-01/24038 | 4/2001 |
| WO | WO-01/33216 | 5/2001 |
| WO | WO-01/52727 | 7/2001 |
| WO | WO-01/52935 | 7/2001 |
| WO | WO-01/54753 | 8/2001 |
| WO | WO-01/57238 | 8/2001 |
| WO | WO-01/57239 | 8/2001 |
| WO | WO-01/67009 | 9/2001 |
| WO | WO-02/13686 | 2/2002 |
| WO | WO-02/16905 | 2/2002 |
| WO | WO-02/17210 | 2/2002 |
| WO | WO-02/058537 | 8/2002 |
| WO | WO-02/078512 | 10/2002 |
| WO | WO-03/036583 | 5/2003 |
| WO | WO-03/076893 | 9/2003 |
| WO | WO-03/082091 | 10/2003 |
| WO | WO-2004/061420 | 7/2004 |
| WO | WO-2005/089103 | 9/2005 |
| WO | WO-2006/086423 | 8/2006 |
| WO | WO-2006/118947 | 11/2006 |
| WO | WO-2006/119084 | 11/2006 |
| WO | WO-2007/002189 | 1/2007 |
| WO | WO-2007/016399 | 2/2007 |
| WO | WO-2007/027381 | 3/2007 |
| WO | WO-2007/027788 | 3/2007 |
| WO | WO-2007/041069 | 4/2007 |
| WO | WO-2007/041070 | 4/2007 |
| WO | WO-2007/041072 | 4/2007 |
| WO | WO-2007/041248 | 4/2007 |
| WO | WO-2007/053832 | 5/2007 |
| WO | WO-2007/056638 | 5/2007 |
| WO | WO-2007/120363 | 10/2007 |
| WO | WO-2007/143225 | 12/2007 |

OTHER PUBLICATIONS

Abruna, H. D., et al., "Rectifying Interfaces Using Two-Layer Films of Electrochemically Polymerized Vinylpyridine and Vinylbipyridine Complexes of Ruthenium and Iron on Electrodes", *Journal of the American Chemical Society*, vol. 103, No. 1, 1981, pp. 1-5.

Albery, W. J., et al., "Amperometric Enzyme Electrodes Part II: Conducting Salts as Electrode Materials for the Oxidation of Glucose Oxidase", *Journal of ElectroAnalytical Chemistry*, vol. 194, 1985, pp. 223-235.

Albery, W. J., et al., "Amperometric Enzyme Electrodes", *Philosophical Transactions of The Royal Society of London*, vol. 316, 1987, pp. 107-119.

Alcock, S. J., et al., "Continuous Analyte Monitoring to Aid Clinical Practice", *IEEE Engineering in Medicine and Biology Magazine*, 1994, pp. 319-325.

Anderson, L. B., et al., "Thin-Layer Electrochemistry: Steady-State Methods of Studying Rate Processes", *Journal of ElectroAnalytical Chemistry*, vol. 10, 1965, pp. 295-305.

Armour, J. C., et al., "Application of Chronic Intravascular Blood Glucose Sensor in Dogs", *Diabetes*, vol. 39, 1990, pp. 1519-1526.

Bartlett, P. N., et al., "Covalent Binding of Electron Relays to Glucose Oxidase", *Journal of the Chemical Society, Chemical Communications*, 1987, pp. 1603-1604.

Bartlett, P. N., et al., "Modification of Glucose Oxidase by Tetrathiafulvalene", *Journal of the Chemical Society, Chemical Communications*, 1990, pp. 1135-1136.

Bartlett, P. N., et al., "Strategies for the Development of Amperometric Enzyme Electrodes", *Biosensors*, vol. 3, 1987/88, pp. 359-379.

Bennion, N., et al., "Alternate Site Glucose Testing: A Crossover Design", *Diabetes Technology & Therapeutics*, vol. 4, No. 1, 2002, pp. 25-33.

Bindra, D. S., et al., "Design and in Vitro Studies of a Needle-Type Glucose Sensor for Subcutaneous Monitoring", *Analytical Chemistry*, vol. 63, No. 17, 1991, pp. 1692-1696.

Blank, T. B., et al., "Clinical Results From a Non-Invasive Blood Glucose Monitor", *Optical Diagnostics and Sensing of Biological Fluids and Glucose and Cholesterol Monitoring II, Proceedings of SPIE*, vol. 4624, 2002, pp. 1-10.

Bobbioni-Harsch, E., et al., "Lifespan of Subcutaneous Glucose Sensors and Their Performances During Dynamic Glycaemia Changes in Rats", *Journal of Biomedical Engineering*, vol. 15, 1993, pp. 457-463.

Boedeker Plastics, Inc., "Polyethylene Specifications", *Web Page of Boedeker.com*, 2007, pp. 1-3.

Brandt, J., et al., "Covalent Attachment of Proteins to Polysaccharide Carriers by Means of Benzoquinone", *Biochimica et Biophysica Acta*, vol. 386, 1975, pp. 196-202.

Brooks, S. L., et al., "Development of an On-Line Glucose Sensor for Fermentation Monitoring", *Biosensors*, vol. 3, 1987/88, pp. 45-56.

Brownlee, M., et al., "A Glucose-Controlled Insulin-Delivery System: Semisynthetic Insulin Bound to Lectin", *Science*, vol. 206, 1979, 1190-1191.

Cass, A. E., et al., "Ferricinum Ion As An Electron Acceptor for Oxido-Reductases", *Journal of ElectroAnalytical Chemistry*, vol. 190, 1985, pp. 117-127.

Cass, A. E., et al., "Ferrocene-Mediated Enzyme Electrode for Amperometric Determination of Glucose", *Analytical Chemistry*, vol. 56, No. 4, 1984, 667-671.

Castner, J. F., et al., "Mass Transport and Reaction Kinetic Parameters Determined Electrochemically for Immobilized Glucose Oxidase", *Biochemistry*, vol. 23 No. 10, 1984, 2203-2210.

Claremont, D. J., et al., "Biosensors for Continuous In Vivo Glucose Monitoring", *Proceedings of the Annual International Conference of the IEEE Engineering in Medicine and Biology Society*, vol. 10, 1988.

Clark Jr., L. C., et al., "Differential Anodic Enzyme Polarography for the Measurement of Glucose", *Oxygen Transport to Tissue: Instrumentation, Methods, and Physiology*, 1973, pp. 127-133.

Clark Jr., L. C., et al., "Electrode Systems for Continuous Monitoring in Cardiovascular Surgery", *Annals New York Academy of Sciences*, 1962, pp. 29-45.

Clark Jr., L. C., et al., "Long-term Stability of Electroenzymatic Glucose Sensors Implanted in Mice", *American Society of Artificial Internal Organs Transactions*, vol. XXXIV, 1998, pp. 259-265.

Clarke, W. L., et al., "Evaluating Clinical Accuracy of Systems for Self-Monitoring of Blood Glucose", *Diabetes Care*, vol. 10, No. 5, 1987, pp. 622-628.

Complaint, "*Abbott Diabetes Care, Inc. v. Dexcom, Inc.*", filed Aug. 11, 2005.

Complaint, Amended, "*Abbott Diabetes Care, Inc. v. Dexcom, Inc.*", filed Jun. 27, 2006.

Csoregi, E., et al., "Design and Optimization of a Selective Subcutaneously Implantable Glucose Electrode Based on 'Wired' Glucose Oxidase", *Analytical Chemistry*, vol. 67, No. 7, 1995, pp. 1240-1244.

Csoregi, E., et al., "Design, Characterization, and One-Point in Vivo Calibration of a Subcutaneously Implanted Glucose Electrode", *Analytical Chemistry*, vol. 66 No. 19, 1994, pp. 3131-3138.

Csoregi, E., et al., "On-Line Glucose Monitoring by Using Microdialysis Sampling and Amperometric Detection Based on 'Wired' Glucose Oxidase in Carbon Paste", *Mikrochimica Acta*, vol. 121, 1995, pp. 31-40.

Dai, W. S., et al., "Hydrogel Membranes with Mesh Size Asymmetry Based on the Gradient Crosslinking of Poly(vinyl alcohol)," *Journal of Membrane Science*, vol. 156, 1999, pp. 67-79.

Davis, G., "Electrochemical Techniques for the Development of Amperometric Biosensors", *Biosensors*, vol. 1, 1985, pp. 161-178.

Degani, Y., et al., "Direct Electrical Communication Between Chemically Modified Enzymes and Metal Electrodes. 1. Electron Transfer from Glucose Oxidase to Metal Electrodes via Electron Relays, Bound Covalently to the Enzyme", *The Journal of Physical Chemistry*, vol. 91, No. 6, 1987, pp. 1285-1289.

Degani, Y., et al., "Direct Electrical Communication Between Chemically Modified Enzymes and Metal Electrodes. 2. Methods for Bonding Electron-Transfer Relays to Glucose Oxidase and D-Amino-Acid Oxidase", *Journal of the American Chemical Society*, vol. 110, No. 8, 1988, pp. 2615-2620.

Degani, Y., et al., "Electrical Communication Between Redox Centers of Glucose Oxidase and Electrodes via Electrostatically and Covalently Bound Redox Polymers", *Journal of the American Chemical Society*, vol. 111, 1989, pp. 2357-2358.

Denisevich, P., et al., "Unidirectional Current Flow and Charge State Trapping at Redox Polymer Interfaces on Bilayer Electrodes: Principles, Experimental Demonstration, and Theory", *Journal of the American Chemical Society*, vol. 103, 1981, pp. 4727-4737.

Dicks, J. M., et al., "Ferrocene Modified Polypyrrole with Immobilised Glucose Oxidase and its Application in Amperometric Glucose Microbiosensors", *Annales de Biologic Clinique*, vol. 47, 1989, pp. 607-619.

Ellis, C. D., et al., "Selectivity and Directed Charge Transfer through an Electroactive Metallopolymer Film", *Journal of the American Chemical Society*, vol. 103, No. 25, 1981, pp. 7480-7483.

Engstrom, R. C., "Electrochemical Pretreatment of Glassy Carbon Electrodes", *Analytical Chemistry*, vol. 54, No. 13, 1982, pp. 2310-2314.

Engstrom, R. C., et al., "Characterization of Electrochemically Pretreated Glassy Carbon Electrodes", *Analytical Chemistry*, vol. 56, No. 2, 1984, pp. 136-141.

Feldman, B., et al., "A Continuous Glucose Sensor Based on Wired Enzyme™ Technology—Results from a 3-Day Trial in Patients with Type 1 Diabetes", *Diabetes Technology & Therapeutics*, vol. 5, No. 5, 2003, pp. 769-779.

Feldman, B., et al., "Electron Transfer Kinetics at Redox Polymer/Solution Interfaces Using Microelectrodes and Twin Electrode Thin Layer Cells", *Journal of ElectroAnalytical Chemistry*, vol. 194, 1985, pp. 63-81.

Fischer, H., et al., "Intramolecular Electron Transfer Medicated by 4,4'-Bypyridine and Related Bridging Groups", *Journal of the American Chemical Society*, vol. 98, No. 18, 1976, pp. 5512-5517.

Flentge, F., et al., "An Enzyme-Reactor for Electrochemical Monitoring of Choline and Acetylcholine: Applications in High-Performance Liquid Chromatography, Bran Tissue, Microdialysis and Cerebrospinal Fluid," *Analytical Biochemistry*, vol. 204, 1992, pp. 305-310.

Foulds, N. C., et al., "Enzyme Entrapment in Electrically Conducting Polymers: Immobilisation of Glucose Oxidase in Polypyrrole and its Application in Amperometric Glucose Sensors", *Journal of the Chemical Society, Faraday Transactions 1*, vol. 82, 1986, pp. 1259-1264.

Foulds, N. C., et al, "Immobilization of Glucose Oxidase in Ferrocene-Modified Pyrrole Polymers", *Analytical Chemistry*, vol. 60, No. 22, 1988, pp. 2473-2478.

Frew, J. E., et al., "Electron-Transfer Biosensors", *Philosophical Transactions of The Royal Society of London*, vol. 316, 1987, pp. 95-106.

Godsland, I. F., et al., "Maximizing the Success Rate of Minimal Model Insulin Sensitivity Measurement in Humans: The Importance of Basal Glucose Levels," *Clinical Science*, vol. 101, 2001, pp. 1-9.

Gorton, L., et al., "Selective Detection in Flow Analysis Based on the Combination of Immobilized Enzymes and Chemically Modified Electrodes", *Analytica Chimica Acta*, vol. 250, 1991, pp. 203-248.

Graham, N. B., "Poly(ethylene oxide) and Related Hydrogels," *Hydrogels in Medicine and Pharmacy, vol. II: Polymers*, Chapter 4, 1987, pp. 95-113.

Gregg, B. A., et al., "Cross-Linked Redox Gels Containing Glucose Oxidase for Amperometric Bionsensor Applications", *Analytical Chemistry*, vol. 62, No. 3, 1990, pp. 258-263.

Gregg, B. A., et al., "Redox Polymer Films Containing Enzymes. 1. A Redox-Conducting Epoxy Cement: Synthesis, Characterization, and Electrocatalytic Oxidation of Hydroquinone", *Journal of Physical Chemistry*, vol. 95, No. 15, 1991, 5970-5975.

Hale, P. D., et al., "A New Class of Amperometric Biosensor Incorporating a Polymeric Electron-Transfer Mediator", *Journal of the American Chemical Society*, vol. 111, No. 9, 1989, pp. 3482-3484.

Harrison, D. J., et al., "Characterization of Perfluorosulfonic Acid Polymer Coated Enzyme Electrodes and a Miniatureized Integrated Potentiostat for Glucose Analysis in Whole Blood", *Analytical Chemistry*, vol. 60, No. 19, 1988, pp. 2002-2007.

Hawkridge, F. M., et al., "Indirect Coulometric Titration of Biological Electron Transport Components", *Analytical Chemistry*, vol. 45, No. 7, 1973, pp. 1021-1027.

Heller, A., "Electrical Connection Enzyme Redox Centers to Electrodes", *Journal of Physical Chemistry*, vol. 96, No. 9, 1990, pp. 3579-3587.

Heller, A., "Electrical Wiring of Redox Enzymes", *Accounts of Chemical Research* vol. 23, No. 5, 1990, 128-134.

Heller, A., et al., "Amperometric Biosensors Based on Three-Dimensional Hydrogel-Forming Epoxy Networks", *Sensors and Actuators B*, vol. 13-14, 1993, pp. 180-183.

Ianniello, R. M., et al., "Differential Pulse Voltammetric Study of Direct Electron Transfer in Glucose Oxidase Chemically Modified Graphite Electrodes", *Analytical Chemistry*, vol. 54, No. 7, 1982, pp. 1098-1101.

Ianniello, R. M., et al , "Immobilized Enzyme Chemically Modified Electrode as an Amperometric Sensor", *Analytical Chemistry*, vol. 53, No. 13, 1981, pp. 2090-2095.

Ikeda, T., et al., "Glucose Oxidase-Immobilized Benzoquinone-Carbon Paste Electrode as a Glucose Sensor", *Agricultural and Biological Chemistry*, vol. 49, No. 2, 1985, pp. 541-543.

Ikeda, T., et al., "Kinetics of Outer-Sphere Electron Transfers Between Metal Complexes in Solutions and Polymeric Films on Modified Electrodes", *Journal of the American Chemical Society*, vol. 103, No. 25, 1981, pp. 7422-7425.

Isermann, R., "Supervision, Fault-Detection and Fault-Diagnosis Methods—An Introduction", *Control Engineering Practice*, vol. 5, No. 5, 1997, pp. 639-652.

Isermann, R., et al., "Trends in the Application of Model-Based Fault Detection and Diagnosis of Technical Processes", *Control Engineering Practice*, vol. 5, No. 5, 1997, pp. 709-719.

Johnson, J. M., et al., "Potential-Dependent Enzymatic Activity in an Enzyme Thin-Layer Cell", *Analytical Chemistry*, vol. 54, No. 8, 1982, pp. 1377-1383.

Johnson, K. W., "Reproducible Electrodeposition of Biomolecules for the Fabrication of Miniature Electroenzymatic Biosensors", *Sensors and Actuators B*, vol. 5, 1991, pp. 85-89.

Johnson, K. W., et al., "In vivo Evaluation of an Electroenzymatic Glucose Sensor Implanted in Subcutaneous Tissue", *Biosensors & Bioelectronics*, vol. 7, 1992, pp. 709-714.

Johnson, P. C., "Peripheral Circulation", *John Wiley & Sons*, 1978, pp. 198.

Jonsson, G., et al., "An Amperometric Glucose Sensor Made by Modification of a Graphite Electrode Surface With Immobilized Glucose Oxidase and Adsorbed Mediator", *Biosensors*, vol. 1, 1985, pp. 355-368.

Josowicz, M., et al., "Electrochemical Pretreatment of Thin Film Platinum Electrodes", *Journal of the Electrochemical Society*, vol. 135 No. 1, 1988, pp. 112-115.

Jungheim, K., et al., "Risky Delay of Hypoglycemia Detection by Glucose Monitoring at the Arm", *Diabetes Care*, vol. 24, No. 7, 2001, pp. 1303-1304.

Kaplan, S. M., "Wiley Electrical and Electronics Engineering Dictionary", *IEEE Press*, 2004, pp. 141, 142, 548, 549.

Katakis, I., et al., "Electrostatic Control of the Electron Transfer Enabling Binding of Recombinant Glucose Oxidase and Redox Polyelectrolytes", *Journal of the American Chemical Society*, vol. 116, No. 8, 1994, pp. 3617-3618.

Katakis, I., et al., "L-α-Glycerophosphate and L-Lactate Electrodes Based on the Electrochemical 'Wiring' of Oxidases", *Analytical Chemistry*, vol. 64, No. 9, 1992, pp. 1008-1013.

Kemp, G. J., "Theoretical Aspects of One-Point Calibration: Causes and Effects of Some Potential Errors, and Their Dependence on Concentration," *Clinical Chemistry*, vol. 30, No. 7, 1984, pp. 1163-1167.

Kenausis, G., et al., "'Wiring' of Glucose Oxidase and Lactate Oxidase Within a Hydrogel Made with Poly(vinyl pyridine) complexed with $[Os(4,4'\text{-dimethoxy-}2,2'\text{-bipyridine})_2Cl]^{+/2+}$", *Journal of the Chemical Society, Faraday Transactions*, vol. 92, No. 20, 1996, pp. 4131-4136.

Kerner, W., et al., "The Function of a Hydrogen Peroxide-Detecting Electroenzymatic Glucose Electrode is Markedly Impaired in Human Subcutaneous Tissue and Plasma," *Biosensors & Bioelectronics*, vol. 8, 1993, pp. 473-482.

Korf, J., et al., "Monitoring of Glucose and Lactate Using Microdialysis: Applications in Neonates and Rat Brain," *Developmental Neuroscience*, vol. 15, 1993, pp. 240-246.

Koudelka, M., et al., "In-Vivo Behaviour of Hypodermically Implanted Microfabricated Glucose Sensors", *Biosensors & Bioelectronics*, vol. 6, 1991, pp. 31-36.

Kulys, J., et al., "Mediatorless Peroxidase Electrode and Preparation of Bienzyme Sensors", *Bioelectrochemistry and Bioenergetics*, vol. 24, 1990, pp. 305-311.

Lager, W., et al., "Implantable Electrocatalytic Glucose Sensor", *Hormone Metabolic Research*, vol. 26, 1994, pp. 526-530.

Laurell, T., "A Continuous Glucose Monitoring System Based on Microdialysis", *Journal of Medical Engineering & Technology*, vol. 16, No. 5, 1992, pp. 187-193.

Lindner, E., et al., "Flexible (Kapton-Based) Microsensor Arrays of High Stability for Cardiovascular Applications", *Journal of the Chemical Society, Faraday Transactions*, vol. 89, No. 2, 1993, pp. 361-367.

Lortz, J., et al., "What is Bluetooth? We Explain The Newest Short-Range Connectivity Technology", *Smart Computing Learning Series, Wireless Computing*, vol. 8, Issue 5, 2002, pp. 72-74.

Maidan, R., et al., "Elimination of Electrooxidizable Interferant-Produced Currents in Amperometric Biosensors", *Analytical Chemistry*, vol. 64, No. 23, 1992, pp. 2889-2896.

Malin, S. F., et al., "Noninvasive Prediction of Glucose by Near-Infrared Diffuse Reflectance Spectoscopy", *Clinical Chemistry*, vol. 45, No. 9, 1999, pp. 1651-1658.

Marko-Varga, G., et al., "Enzyme-Based Biosensor as a Selective Detection Unit in Column Liquid Chromatography", *Journal of Chromatography A*, vol. 660, 1994, pp. 153-167.

Mastrototaro, J. J., et al., "An Electroenzymatic Glucose Sensor Fabricated on a Flexible Substrate", *Sensors and Actuators B*, vol. 5, 1991, pp. 139-144.

Mauras, N., et al., "Lack of Accuracy of Continuous Glucose Sensors in Healthy, Nondiabetic Children: Results of the Diabetes Research in Children Network (DirecNet) Accuracy Study," *Journal of Pediatrics*, 2004, pp. 770-775.

McGarraugh, G., et al., "Physiological Influences on Off-Finger Glucose Testing", *Diabetes Technology & Therapeutics*, vol. 3, No. 3, 2001, pp. 367-376.

McKean, B. D., et al., "A Telemetry-Instrumentation System for Chronically Implanted Glucose and Oxygen Sensors", *IEEE Transactions on Biomedical Engineering*, vol. 35, No. 7, 1988, pp. 526-532.

McNeil, C. J., et al., "Thermostable Reduced Nicotinamide Adenine Dinucleotide Oxidase: Application to Amperometric Enzyme Assay", *Analytical Chemistry*, vol. 61, No. 1, 1989, pp. 25-29.

Miyawaki, O., et al., "Electrochemical and Glucose Oxidase Coenzyme Activity of Flavin Adenine Dinucleotide Covalently Attached to Glassy Carbon at the Adenine Amino Group", *Biochimica et Biophysica Acta*, vol. 838, 1985, pp. 60-68.

Moatti-Sirat, D., et al., "Evaluating In Vitro and In Vivo the Interference of Ascorbate and Acetaminophen on Glucose Detection by a Needle-Type Glucose Sensor", *Biosensors & Bioelectronics*, vol. 7, 1992, pp. 345-352.

Moatti-Sirat, D., et al., "Reduction of Acetaminophen Interference in Glucose Sensors by a Composite Nafion Membrane: Demonstration in Rats and Man", *Diabetologia*, vol. 37, 1994, pp. 610-616.

Moatti-Sirat, D., et al., "Towards Continuous Glucose Monitoring: In Vivo Evaluation of a Miniaturized Glucose Sensor Implanted for Several Days in Rat Subcutaneous Tissue", *Diabetologia*, vol. 35, 1992, pp. 224-330.

Nagy, G., et al., "A New Type of Enzyme Electrode: The Ascorbic Acid Eliminator Electrode", *Life Sciences*, vol. 31, No. 23, 1982, pp. 2611-2616.

Nakamura, S., et al., "Effect of Periodate Oxidation on the Structure and Properties of Glucose Oxidase", *Biochimica et Biophysica Acta.*, vol. 445, 1976, pp. 294-308.

Narasimham, K., et al., "p-Benzoquinone Activation of Metal Oxide Electrodes for Attachment of Enzymes", *Enzyme and Microbial Technology*, vol. 7, 1985, pp. 283-286.

Ohara, T. J., "Osmium Bipyridyl Redox Polymers Used in Enzyme Electrodes", *Platinum Metals Review*, vol. 39, No. 2, 1995, pp. 54-62.

Ohara, T. J., et al., "'Wired' Enzyme Electrodes for Amperometric Determination of Glucose or Lactate in the Presence of Interfering Substances", *Analytical Chemistry*, vol. 66, No. 15, 1994, pp. 2451-2457.

Ohara, T. J., et al., "Glucose Electrodes Based on Cross-Linked $[Os(bpy)_2Cl]^{+/2+}$ Complexed Poly(1-Vinylimidazole) Films", *Analytical Chemistry*, vol. 65, No. 23, 1993, pp. 3512-3517.

Olievier, C. N., et al., "In Vivo Measurement of Carbon Dioxide Tension with a Miniature Electrodes", *Pflugers Archiv: European Journal of Physiology*, vol. 373, 1978, pp. 269-272.

Paddock, R. M., et al., "Electrocatalytic Reduction of Hydrogen Peroxide via Direct Electron Transfer From Pyrolytic Graphite Electrodes to Irreversibly Adsorbed Cyctochrome C Peroxidase", *Journal of ElectroAnalytical Chemistry*, vol. 260, 1989, pp. 487-494.

Palleschi, G., et al., "A Study of Interferences in Glucose Measurements in Blood by Hydrogen Peroxide Based Glucose Probes", *Analytical Biochemistry*, vol. 159, 1986, pp. 114-121.

Pankratov, I., et al., "Sol-Gel Derived Renewable-Surface Biosensors", *Journal of ElectroAnalytical Chemistry*, vol. 393, 1995, pp. 35-41.

Pathak, C., et al., "Rapid Photopolymerization of Immunoprotective Gels in Contact with Cells and Tissue", *Journal of the American Chemical Society*, vol. 114, No. 21, 1992, pp. 8311-8312.

Pickup, J., "Developing Glucose Sensors for In Vivo Use", *Tibtech*, vol. 11, 1993, pp. 285-291.

Pickup, J., et al., "Implantable Glucose Sensors: Choosing the Appropriate Sensing Strategy", *Biosensors*, vol. 3, 1987/88, pp. 335-346.

Pickup, J., et al., "In Vivo Molecular Sensing in Diabetes Mellitus: An Implantable Glucose Sensor with Direct Electron Transfer", *Diabetologia*, vol. 32, 1989, pp. 213-217.

Pickup, J., et al., "Potentially-Implantable, Amperometric Glucose Sensors with Mediated Electron Transfer: Improving the Operating Stability", *Biosensors*, vol. 4, 1989, pp. 109-119.

Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268-2272.

Poitout, V., et al., "A Glucose Monitoring System for On Line Estimation in Man of Blood Glucose Concentration Using a Miniaturized Glucose Sensor Implanted in the Subcutaneous Tissue and a Wearable Control Unit", *Diabetolgia*, vol. 36, 1993, pp. 658-663.

Poitout, V., et al., "Calibration in Dogs of a Subcutaneous Miniaturized Glucose Sensor Using a Glucose Meter for Blood Glucose Determination", *Biosensors & Bioelectronics*, vol. 7, 1992, pp. 587-592.

Poitout, V., et al., "In Vitro and In Vivo Evaluation in Dogs of a Miniaturized Glucose Sensor", *Asaio Transactions*, vol. 37, No. 3, 1991, pp. M298-M300.

Pollak, A., et al., "Enzyme Immobilization by Condensation Copolymerization into Cross-Linked Polyacrylamide Gels", *Journal of the American Chemical Society*, vol. 102, No. 20, 1980, pp. 6324-6336.

Quinn, C. P., et al., "Kinetics of Glucose Delivery to Subcutaneous Tissue in Rats Measured with 0.3-mm Amperometric Microsensors", *The American Physiological Society*, 1995, E155-E161.

Reach, G., et al., "Can Continuous Glucose Monitoring Be Used for the Treatment of Diabetes?", *Analytical Chemistry*, vol. 64, No. 6, 1992, pp. 381-386.

Rebrin, K., et al., "Automated Feedback Control of Subcutaneous Glucose Concentration in Diabetic Dogs", *Diabetologia*, vol. 32, 1989, pp. 573-576.

Reusch, W., "Other Topics: Organometallic Chemistry: Organometallic Compounds: Main Group Organometallic Compounds," *Virtual Textbook of Organic Chemistry*, 1999, Rev. 2007, 25 pages.

Roe, J. N., et al., "Bloodless Glucose Measurements", *Critical Review in Therapeutic Drug Carrier Systems*, vol. 15, Issue 3, 1998, pp. 199-241.

Sacks (ED), "Guidelines and Recommendations for Laboratory Analysis in the Diagnosis and Management of Diabetes Mellitus," *The National Academy of Clinical Biochemistry Presents Laboratory Medicine Practice Guidelines*, vol. 13, 2002, pp. 8-11, 21-23, 52-56, 63.

Sakakida, M., et al., "Development of Ferrocene-Mediated Needle-Type Glucose Sensor as a Measure of True Subcutaneous Tissue Glucose Concentrations", *Artificial Organs Today*, vol. 2, No. 2, 1992, pp. 145-158.

Sakakida, M., et al., "Ferrocene-Mediated Needle-Type Glucose Sensor Covered with Newly Designed Biocompatible Membrane", *Sensors and Actuators B*, vol. 13-14, 1993, pp. 319-322.

Salehi, C., et al., "A Telemetry-Instrumentation System for Long-Term Implantable Glucose and Oxygen Sensors", *Analytical Letters*, vol. 29, No. 13, 1996, pp. 2289-2308.

Samuels, G. J., et al., "An Electrode-Supported Oxidation Catalyst Based on Ruthenium (IV). pH 'Encapsulation' in a Polymer Film", *Journal of the American Chemical Society*, vol. 103, No. 2, 1981, pp. 307-312.

Sasso, S. V., et al., "Electropolymerized 1,2-Diaminobenzene as a Means to Prevent Interferences and Fouling and to Stabilize Immobilized Enzyme in Electrochemical Biosensors", *Analytical Chemistry*, vol. 62, No. 11, 1990, pp. 1111-1117.

Scheller, F. W., et al., "Second Generation Biosensors," *Biosensors & Bioelectronics*, vol. 6, 1991, pp. 245-253.

Scheller, F., et al., "Enzyme Electrodes and Their Application", *Philosophical Transactions of The Royal Society of London B*, vol. 316, 1987, pp. 85-94.

Schmehl, R. H., et al., "The Effect of Redox Site Concentration on the Rate of Mediated Oxidation of Solution Substrates by a Redox Copolymer Film", *Journal of ElectroAnalytical Chemistry*, vol. 152, 1983, pp. 97-109.

Schmidt, F. J., et al., "Calibration of a Wearable Glucose Sensor", *The International Journal of Artificial Organs*, vol. 15, No. 1, 1992, pp. 55-61.

Schmidtke, D. W., et al., "Measurement and Modeling of the Transient Difference Between Blood and Subcutaneous Glucose Concentrations in the Rat After Injection of Insulin", *Proceedings of the National Academy of Sciences*, vol. 95, 1998, pp. 294-299.

Shaw, G. W., et al., "In Vitro Testing of a Simply Constructed, Highly Stable Glucose Sensor Suitable for Implantation in Diabetic Patients", *Biosensors & Bioelectronics*, vol. 6, 1991, pp. 401-406.

Shichiri, M., et al., "Glycaemic Control in Pancreatectomized Dogs with a Wearable Artificial Endocrine Pancreas", *Diabetologia*, vol. 24, 1983, pp. 179-184.

Shichiri, M., et al., "In Vivo Characteristics of Needle-Type Glucose Sensor—Measurements of Subcutaneous Glucose Concentrations in Human Volunteers", *Hormone and Metabolic Research Supplement Series*, vol. 20, 1988, pp. 17-20.

Shichiri, M., et al., "Membrane Design for Extending the Long-Life of an Implantable Glucose Sensor", *Diabetes Nutrition and Metabolism*, vol. 2, 1989, pp. 309-313.

Shichiri, M., et al., "Needle-type Glucose Sensor for Wearable Artificial Endocrine Pancreas", *Implantable Sensors for Closed-Loop Prosthetic Systems*, Chapter 15, 1985, pp. 197-210.

Shichiri, M., et al., "Telemetry Glucose Monitoring Device With Needle-Type Glucose Sensor: A Useful Tool for Blood Glucose Monitoring in Diabetic Individuals", *Diabetes Care*, vol. 9, No. 3, 1986, pp. 298-301.

Shichiri, M., et al., "Wearable Artificial Endocrine Pancreas With Needle-Type Glucose Sensor", *The Lancet*, 1982, pp. 1129-1131.

Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp. 937-942.

Sittampalam, G., et al., "Surface-Modified Electrochemical Detector for Liquid Chromatography", *Analytical Chemistry*, vol. 55, No. 9, 1983, pp. 1608-1610.

Skoog, D. A., et al., "Evaluation of Analytical Data," *Fundamentals of Analytical Chemistry*, 1966, pp. 55.

Soegijoko, S., et al., "External Artificial Pancreas: A New Control Unit Using Microprocessor", *Hormone and Metabolic Research Supplement Series*, vol. 12, 1982, pp. 165-169.

Sprules, S. D., et al., "Evaluation of a New Disposable Screen-Printed Sensor Strip for the Measurement of NADH and Its Modification to Produce a Lactate Biosensor Employing Microliter Volumes", *Electroanalysis*, vol. 8, No. 6, 1996, pp. 539-543.

Sternberg, F., et al., "Calibration Problems of Subcutaneous Glucosensors when Applied 'In-Situ' in Man", *Hormone and Metabolic Research*, vol. 26, 1994, pp. 523-526.

Sternberg, R., et al., "Covalent Enzyme Coupling on Cellulose Acetate Membranes for Glucose Sensor Development", *Analytical Chemistry*, vol. 60, No. 24, 1988, pp. 2781-2786.

Sternberg, R., et al., "Study and Development of Multilayer Needle-Type Enzyme-Based Glucose Microsensors", *Biosensors*, vol. 4, 1988, pp. 27-40.

Suekane, M, "Immobilization of Glucose Isomerase", *Zettschrift fur Allgemeine Mikrobiologie*, vol. 22, No. 8, 1982, pp. 565-576.

Tajima, S., et al., "Simultaneous Determination of Glucose and 1,5-Anydroglucitol", *Chemical Abstracts*, vol. 111, No. 25, 1989, pp. 394.

Takamura, A., et al., Drug release from Poly(vinyl alcohol) Gel Prepared by Freeze-Thaw Procedure, *Journal of Controlled Release*, vol. 20, 1992, pp. 21-27.

Tarasevich, M. R., "Bioelectrocatalysis", *Comprehensive Treatise of Electrochemistry*, vol. 10, 1985, pp. 231-295.

Tatsuma, T., et al., "Enzyme Monolayer—and Bilayer-Modified Tin Oxide Electrodes for the Determination of Hydrogen Peroxide and Glucose", *Analytical Chemistry*, vol. 61, No. 21, 1989, pp. 2352-2355.

Taylor, C., et al., "'Wiring' of Glucose Oxidase Within a Hydrogel Made with Polyvinyl Imidazole Complexed with [(Os-4,4'-dimethoxy-2,2'-bipyridine)Cl]$^{+/2+}$", *Journal of ElectroAnalytical Chemistry*, vol. 396, 1995, pp. 511-515.

Thompson, M., et al., "In Vivo Probes: Problems and Perspectives", *Clinical Biochemistry*, vol. 19, 1986, pp. 255-261.

Travenol Laboratories, Inc., *An Introduction to "Eugly"*, Book 1, 1985, pp. 1-22.

Trojanowicz, M., et al., "Enzyme Entrapped Polypyrrole Modified Electrode for Flow-Injection Determination of Glucose", *Biosensors & Bioelectronics*, vol. 5, 1990, pp. 149-156.

Tsalikian, E., et al., "Accuracy of the GlucoWatch G2® Biographer and the Continuous Glucose Monitoring System During Hypoglycemia: Experience of the Diabetes Research in Children Network", *Diabetes Care*, vol. 27, No. 3, 2004, pp. 722-726.

Turner, A., et al., "Diabetes Mellitus: Biosensors for Research and Management", *Biosensors*, vol. 1, 1985, pp. 85-115.

Turner, R. F., et al., "A Biocompatible Enzyme Electrode for Continuous in vivo Glucose Monitoring in Whole Blood", *Sensors and Actuators B*, vol. 1, 1990, pp. 561-564.

Tuzhi, P., et al., "Constant Potential Pretreatment of Carbon Fiber Electrodes for In Vivo Electrochemistry", *Analytical Letters*, vol. 24, No. 6, 1991, pp. 935-945.

U.S. Appl. No. 90/007,903, Request for Reexamination of U.S. Patent No. 6,565,509, filed Jan. 25, 2006.

U.S. Appl. No. 90/007,910, Request for Reexamination of U.S. Patent No. 6,175,752, filed Feb. 1, 2006.

U.S. Appl. No. 90/007,913, Request for Reexamination of U.S. Patent No. 6,284,478, filed Feb. 1, 2006.

U.S. Appl. No. 90/007,914, Request for Reexamination of U.S. Patent No. 6,329,161, filed Feb. 1, 2006.

U.S. Appl. No. 90/008,172, Request for Reexamination of U.S. Patent No. 6,990,366, filed Aug. 16, 2006.

U.S. Appl. No. 90/008,173, Request for Reexamination of U.S. Patent No. 6,134,461, filed Aug. 16, 2006.

U.S. Appl. No. 90/008,457, Request for Reexamination of U.S. Patent No. 6,990,366, filed Jan. 23, 2007.

U.S. Appl. No. 90/008,665, Request for Reexamination of U.S. Patent No. 6,284,478, filed May 25, 2007.

U.S. Appl. No. 90/008,713, Request for Reexamination of U.S. Patent No. 6,329,161, filed Jul. 25, 2007.

Umana, M., "Protein-Modified Electrochemically Active Biomaterial Surface", *U.S. Army Research Office, Analytical and Chemical Sciences Research Triangle Institute*, 1988, pp. 1-9.

Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring*, Chapter 4, 1997, pp. 117-137.

Urban, G., et al., "Miniaturized Thin-Film Biosensors Using Covalently Immobilized Glucose Oxidase", *Biosensors & Bioelectronics*, vol. 6, 1991, pp. 555-562.

Velho, G., et al., "In Vitro and In Vivo Stability of Electrode Potentials in Needle-Type Glucose Sensors", *Diabetes*, vol. 38, No. 2, 1989, pp. 164-171.

Velho, G., et al., "Strategies for Calibrating a Subcutaneous Glucose Sensor", *Biomedica Biochimica Acta*, vol. 48, 1989, pp. 957-964.

Von Woedtke, T., et al., "In Situ Calibration of Implanted Electrochemical Glucose Sensors", *Biomedica Biochimica Acta*, vol. 48, 1989, pp. 943-952.

Vreeke, M. S., et al., "Hydrogen Peroxide Electrodes Based on Electrical Connection of Redox Centers of Various Peroxidases to Electrodes through a Three-Dimensional Electron-Relaying Polymer Network", *Diagnostic Biosensors Polymers*, Chapter 15, 1993, pp. 180-193.

Vreeke, M., et al., "Hydrogen Peroxide and β-Nicotinamide Adenine Dinucleotide Sensing Amperometric Electrodes Based on Electrical Connection of Horseradish Peroxidase Redox Centers to Electrodes through a Three-Dimensional Electron Relaying Polymer Network", *Analytical Chemistry*, vol. 64, No. 24, 1992, pp. 3084-3090.

Wang, D. L., et al., "Miniaturized Flexible Amperometric Lactate Probe", *Analytical Chemistry*, vol. 65, No. 8, 1993, pp. 1069-1073.

Wang, J., et al., "Activation of Glassy Carbon Electrodes by Alternating Current Electrochemical Treatment", *Analytica Chimica Acta*, vol. 167, 1985, pp. 325-334.

Wang, J., et al., "Amperometric Biosensing of Organic Peroxides with Peroxidase-Modified Electrodes", *Analytica Chimica Acta*, vol. 254, 1991, pp. 81-88.

Wang, J., et al., "Screen-Printable Sol-Gel Enzyme-Containing Carbon Inks", *Analytical Chemistry*, vol. 68, No. 15, 1996, pp. 2705-2708.

Wang, J., et al., "Sol-Gel-Derived Metal-Dispersed Carbon Composite Amperometric Biosensors", *Electroanalysis*, vol. 9, No. 1, 1997, pp. 52-55.

Williams, D. L., et al., "Electrochemical-Enzymatic Analysis of Blood Glucose and Lactate", *Analytical Chemistry*, vol. 42, No. 1, 1970, pp. 118-121.

Wilson, G. S., et al., "Progress Toward the Development of an Implantable Sensor for Glucose", *Clinical Chemistry*, vol. 38, No. 9, 1992, pp. 1613-1617.

Yabuki, S., et al., "Electro-Conductive Enzyme Membrane", *Journal of the Chemical Society, Chemical Communications*, 1989, pp. 945-946.

Yang, C., et al., "A Comparison of Physical Properties and Fuel Cell Performance of Nafion and Zirconium Phosphate/Nafion Composite Membranes," *Journal of Membrane Science*, vol. 237, 2004, pp. 145-161.

Yang, L., et al., "Determination of Oxidase Enzyme Substrates Using Cross-Flow Thin-Layer Amperometry", *Electroanalysis*, vol. 8, No. 8-9, 1996, pp. 716-721.

Yao, S. J., et al., "The Interference of Ascorbate and Urea in Low-Potential Electrochemical Glucose Sensing", *Proceedings of the Twelfth Annual International Conference of the IEEE Engineering in Medicine and Biology Society*, vol. 12, Part 2, 1990, pp. 487-489.

Yao, T., "A Chemically-Modified Enzyme Membrane Electrode as an Amperometric Glucose Sensor", *Analytica Chimica Acta*, vol. 148, 1983, pp. 27-33.

Ye, L., et al., "High Current Density 'Wired' Quinoprotein Glucose Dehydrogenase Electrode", *Analytical Chemistry*, vol. 65, No. 3, 1993, pp. 238-241.

Yildiz, A., et al., "Evaluation of an Improved Thin-Layer Electrode", *Analytical Chemistry*, vol. 40, No. 7, 1968, pp. 1018-1024.

Zamzow, K., et al., "New Wearable Continuous Blood Glucose Monitor (BGM) and Artificial Pancreas (AP)", *Diabetes*, vol. 39, 1990, pp. 5A-20.

Zhang, Y., et al., "Application of Cell Culture Toxicity Tests to the Development of Implantable Biosensors", *Biosensors & Bioelectronics*, vol. 6, 1991, pp. 653-661.

Zhang, Y., et al., "Elimination of the Acetaminophen Interference in an Implantable Glucose Sensor", *Analytical Chemistry*, vol. 66, No. 7, 1994, pp. 1183-1188.

Feldman, B., et al., "Correlation of Glucose Concentrations in Interstitial Fluid and Venous Blood During Periods of Rapid Glucose Change", *Abbott Diabetes Care, Inc. Freestyle Navigator Continuous Glucose Monitor Pamphlet*, 2004.

Hamilton, "Hamilton Needle Gauge Index", www.hamiltoncompany.com, 1998.

Jungheim, K., et al., "How Rapid Does Glucose Concentration Change in Daily Life of Patients with Type 1 Diabetes?", 2002, pp. 250.

McGarraugh, G., et al., "Glucose Measurements Using Blood Extracted from the Forearm and the Finger", *TheraSense, Inc.*, 2001, 16 Pages.

Abstract of Japanese Patent No. JP-55-010581 published Jan. 25, 1980 to Matsushita Electric Industrial Co., Ltd.

Abstract of Japanese Patent No. JP-55-010583 published Jan. 25, 1980 to Matsushita Electric Industrial Co., Ltd.

Abstract of Japanese Patent No. JP-55-010584 published Jan. 25, 1980 to Matsushita Electric Industrial Co., Ltd.

International Preliminary Report on Patentability and Written Opinion of the International Searching Authority for International Application No. PCT/US2007/065500 filed Mar. 29, 2007 to Abbott Diabetes Care, Inc., mailed Oct. 9, 2008.

International Search Report and Written Opinion of the International Searching Authority for International Application No. PCT/US2007/065500 filed Mar. 29, 2007 to Abbott Diabetes Care, Inc.

\* cited by examiner

METHOD AND SYSTEM FOR POWERING AN ELECTRONIC DEVICE

BACKGROUND

Analyte, e.g., glucose monitoring systems including continuous and discrete monitoring systems generally include a battery powered and microprocessor controlled system which is configured to detect signals proportional to the corresponding measured glucose levels using an electrometer, and RF signals to transmit the collected data. One aspect of certain glucose monitoring systems include a transcutaneous or subcutaneous analyte sensor configuration which is, for example, partially mounted on the skin of a subject whose glucose level is to be monitored. The sensor may use a two or three-electrode (work, reference and counter electrodes) configuration driven by a controlled potential (potentiostat) analog circuit connected through a contact system.

The analyte sensor may be configured so that at least a portion thereof is placed under the skin of the patient so as to detect the analyte levels of the patient, and another portion of segment of the analyte sensor that is in communication with the transmitter unit. The transmitter unit is configured to transmit the analyte levels detected by the sensor over a wireless communication link such as an RF (radio frequency) communication link. To transmit signals, the transmitter unit requires a power supply such as a battery. Generally, batteries have a limited life span and require periodic replacement. More specifically, depending on the power consumption of the transmitter unit, the power supply in the transmitter unit may require frequent replacement, or the transmitter unit may require replacement (e.g, disposable power supply such as disposable battery).

In view of the foregoing, it would be desirable to have an approach to provide a power supply for a transmitter unit in a data monitoring and management system.

SUMMARY OF THE INVENTION

In view of the foregoing, in accordance with the various embodiments of the present invention, there is provided a method and apparatus for providing a power supply to an analyte monitoring system, where embodiments include an inductive rechargeable power supply for a data monitoring and management system in which a high frequency magnetic field is generated to provide power supply to a rechargeable power source such as a battery of a transmitter unit in the data monitoring and management system.

These and other objects, features and advantages of the present invention will become more fully apparent from the following detailed description of the embodiments, the appended claims and the accompanying drawings.

DETAILED DESCRIPTION

As described in accordance with the various embodiments of the present invention below, there are provided methods and system for inductively recharging a power source such as a rechargeable battery in an electronic device such as a data transmitter unit used in data monitoring and management systems such as, for example, in glucose monitoring and management systems.

Figure 1:
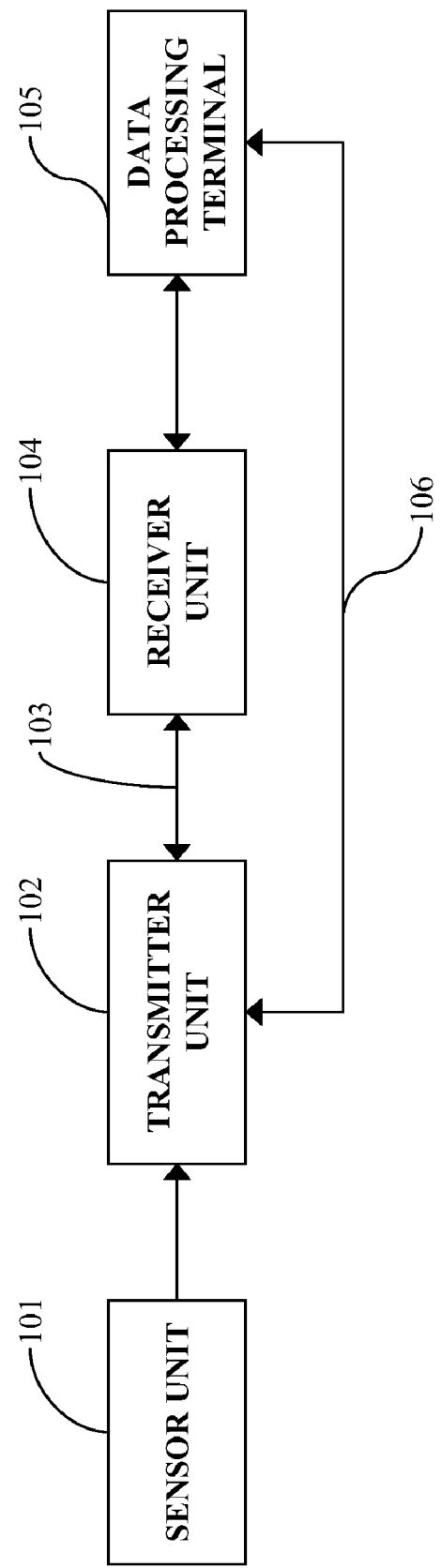
FIG. 1 illustrates a block diagram of a data monitoring and management system for practicing one embodiment of the present invention.

FIG. 1 illustrates a data monitoring and management system such as, for example, an analyte (e.g., glucose) monitoring system 100 in accordance with embodiments of the present invention. The subject invention is further described primarily with respect to a glucose monitoring system for convenience and such description is in no way intended to limit the scope of the invention. It is to be understood that the analyte monitoring system may be configured to monitor a variety of analytes, e.g., lactate, ketones, and the like.

Indeed, analytes that may be monitored include, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored.

The embodiment of glucose monitoring system 100 includes a sensor 101, a transmitter 102 coupled to the sensor 101, and a receiver 104 which is configured to communicate with the transmitter 102 via a communication link 103. The receiver 104 may be further configured to transmit data to a data processing terminal 105 for evaluating the data received by the receiver 104. Moreover, the data processing terminal in one embodiment may be configured to receive data directly from the transmitter 102 via a communication link 106 which may optionally be configured for bi-directional communication. In addition, within the scope of the present invention, the receiver 104 may be configured to include the functions of the data processing terminal 105 such that the receiver 104 may be configured to receive the transmitter data as well as to perform the desired and/or necessary data processing to analyze the received data, for examples.

Only one sensor 101, transmitter 102, communication link 103, receiver 104, and data processing terminal 105 are shown in the embodiment of the glucose monitoring system 100 illustrated in FIG. 1. However, it will be appreciated by one of ordinary skill in the art that the glucose monitoring system 100 may include one or more sensor 101, transmitter 102, communication link 103, receiver 104, and data processing terminal 105, where each receiver 104 is uniquely synchronized with a respective transmitter 102. Moreover, within the scope of the present invention, the glucose monitoring system 100 may be a continuous monitoring system, or semi-continuous, or a discrete monitoring system.

In one embodiment of the present invention, the sensor 101 is physically positioned in or on the body of a user whose glucose level is being monitored. The sensor 101 may be configured to continuously sample the glucose level of the user and convert the sampled glucose level into a corresponding data signal for transmission by the transmitter 102. In one embodiment, the transmitter 102 is mounted on the sensor 101 so that both devices are positioned on the user's body. The transmitter 102 may perform data processing such as filtering and encoding of data signals, each of which corresponds to a sampled glucose level of the user, for transmission to the receiver 104 via the communication link 103.

In one embodiment, the glucose monitoring system 100 is configured as a one-way RF communication path from the transmitter 102 to the receiver 104. In such embodiment, the transmitter 102 transmits the sampled data signals received from the sensor 101 without acknowledgement from the receiver 104 that the transmitted sampled data signals have been received. For example, the transmitter 102 may be configured to transmit the encoded sampled data signals at a fixed rate (e.g., at one minute intervals) after the completion of the initial power on procedure. Likewise, the receiver 104 may be configured to detect such transmitted encoded sampled data signals at predetermined time intervals. Alternatively, the glucose monitoring system 100 may be configured with a bi-directional RF (or otherwise) communication between the transmitter 102 and the receiver 104.

Additionally, in one aspect, the receiver 104 may include two sections. The first section is an analog interface section that is configured to communicate with the transmitter 102 via the communication link 103. In one embodiment, the analog interface section may include an RF receiver and an antenna for receiving and amplifying the data signals from the transmitter 102, which are thereafter, demodulated with a local oscillator and filtered through a band-pass filter. The second section of the receiver 104 is a data processing section which is configured to process the data signals received from the transmitter 102 such as by performing data decoding, error detection and correction, data clock generation, and data bit recovery.

In operation, the receiver 104 is configured to detect the presence of the transmitter 102 within its range based on, for example, the strength of the detected data signals received from the transmitter 102 or a predetermined transmitter identification information. Upon successful synchronization with the corresponding transmitter 102, the receiver 104 is configured to begin receiving from the transmitter 102 data signals corresponding to the user's detected glucose level. More specifically, the receiver 104 in one embodiment is configured to perform synchronized time hopping with the corresponding synchronized transmitter 102 via the communication link 103 to obtain the user's detected glucose level.

Referring again to FIG. 1, the data processing terminal 105 may include a personal computer, a portable computer such as a laptop or a handheld device (e.g., personal digital assistants (PDAs)), and the like, each of which may be configured for data communication with the receiver via a wired or a wireless connection. Additionally, the data processing terminal 105 may further be connected to a data network (not shown) for storing, retrieving and updating data corresponding to the detected glucose level of the user.

Within the scope of the present invention, the data processing terminal 105 may include an infusion device such as an insulin infusion pump or the like, which may be configured to administer insulin to patients, and which may be configured to communicate with the receiver unit 104 for receiving, among others, the measured glucose level. Alternatively, the receiver unit 104 may be integrated with an infusion device so that the receiver unit 104 is configured to administer insulin therapy to patients, for example, for administering and modifying basal profiles, as well as for determining appropriate boluses for administration based on, among others, the detected glucose levels received from the transmitter 102.

Additionally, the transmitter 102, the receiver 104 and the data processing terminal 105 may each be configured for bi-directional wireless communication such that each of the transmitter 102, the receiver 104 and the data processing terminal 105 may be configured to communicate (that is, transmit data to and receive data from) with each other via the wireless communication link 103. More specifically, the data processing terminal 105 may in one embodiment be configured to receive data directly from the transmitter 102 via the communication link 106, where the communication link 106, as described above, may be configured for bi-directional communication.

In this embodiment, the data processing terminal 105 which may include an insulin pump or the like, may be configured to receive the glucose signals from the transmitter 102, and thus, incorporate the functions of the receiver 104 including data processing for managing the patient's insulin therapy and glucose monitoring. In one embodiment, the communication link 103 may include one or more of an RF communication protocol, an infrared communication protocol, a Bluetooth enabled communication protocol, an 802.11x wireless communication protocol, or an equivalent wireless communication protocol which would allow secure, wireless communication of several units (for example, per HIPPA requirements) while avoiding potential data collision and interference.

Figure 2:
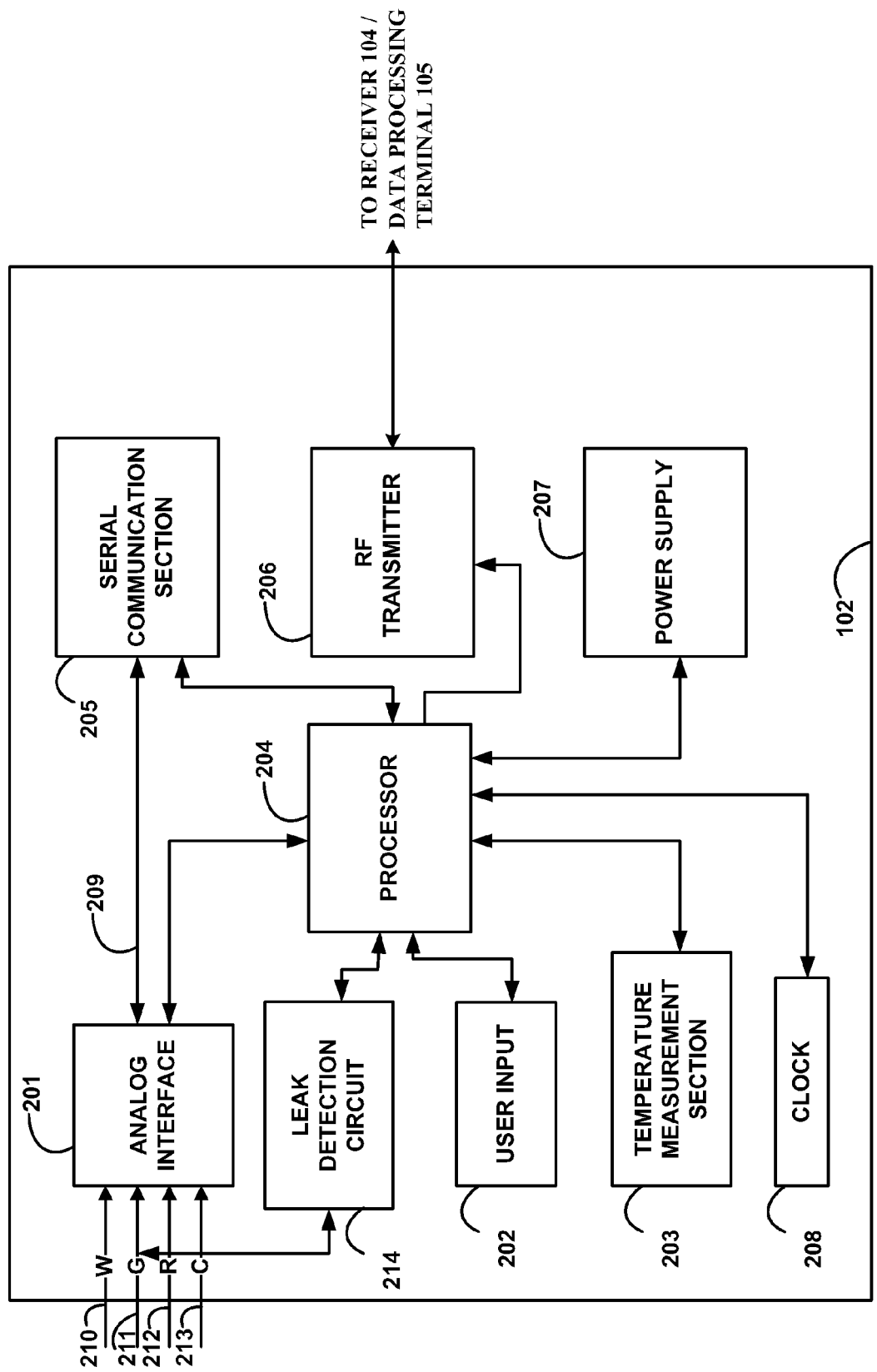
FIG. 2 is a block diagram of the transmitter of the data monitoring and management system shown in FIG. 1 in accordance with one embodiment of the present invention.

FIG. 2 is a block diagram of the transmitter of the data monitoring and detection system shown in FIG. 1 in accordance with one embodiment of the present invention. Referring to the Figure, the transmitter 102 in one embodiment includes one or more of the following components. The transmitter may include an analog interface 201 configured to communicate with the sensor 101 (FIG. 1), a user input 202, and a temperature detection section 203, each of which is operatively coupled to a transmitter processor 204 such as a central processing unit (CPU). As can be seen from FIG. 2, there are provided four contacts, three of which are electrodes—work electrode (W) 210, guard contact (G) 211, reference electrode (R) 212, and counter electrode (C) 213, each operatively coupled to the analog interface 201 of the transmitter 102 for connection to the sensor unit 201 (FIG. 1). In one embodiment, each of the work electrode (W) 210, guard contact (G) 211, reference electrode (R) 212, and counter electrode (C) 213 may be made using a conductive material that is either printed or etched, for example, such as carbon which may be printed, or metal foil (e.g., gold) which may be etched.

Further shown in FIG. 2 are a transmitter serial communication section 205 and an RF transmitter 206, each of which is also operatively coupled to the transmitter processor 204. Moreover, a power supply 207 such as a battery is also provided in the transmitter 102 to provide the necessary power for the transmitter 102. Additionally, as can be seen from the Figure, clock 208 is provided to, among others, supply real time information to the transmitter processor 204.

In one embodiment, a unidirectional input path is established from the sensor 101 (FIG. 1) and/or manufacturing and testing equipment to the analog interface 201 of the transmitter 102, while a unidirectional output is established from the output of the RF transmitter 206 of the transmitter 102 for transmission to the receiver 104. In this manner, a data path is shown in FIG. 2 between the aforementioned unidirectional input and output via a dedicated link 209 from the analog interface 201 to serial communication section 205, thereafter to the processor 204, and then to the RF transmitter 206. As such, in one embodiment, via the data path described above, the transmitter 102 is configured to transmit to the receiver 104 (FIG. 1), via the communication link 103 (FIG. 1), processed and encoded data signals received from the sensor 101 (FIG. 1). Additionally, the unidirectional communication data path between the analog interface 201 and the RF transmitter 206 discussed above allows for the configuration of the transmitter 102 for operation upon completion of the manufacturing process as well as for direct communication for diagnostic and testing purposes.

As discussed above, the transmitter processor 204 is configured to transmit control signals to the various sections of the transmitter 102 during the operation of the transmitter 102. In one embodiment, the transmitter processor 204 also includes a memory (not shown) for storing data such as the identification information for the transmitter 102, as well as the data signals received from the sensor 101. The stored information may be retrieved and processed for transmission to the receiver 104 under the control of the transmitter processor 204. Furthermore, the power supply 207 may include a commercially available battery.

The power supply section 207 provides power to the transmitter for a minimum amount of time, e.g., about three months of continuous operation after having been stored for a certain period of time, e.g., about eighteen months in a low-power (non-operating) mode. It is to be understood that the described three month power supply and eighteen month low-power mode are exemplary only and are in no way intended to limit the invention as the power supply may be less or more than three months and/or the low power mode may be less or more than eighteen months. In one embodiment, this may be achieved by the transmitter processor 204 operating in low power modes in the non-operating state, for example, drawing no more than approximately 1 μA of current. Indeed, in one embodiment, during the manufacturing process of the transmitter 102, the transmitter 102 may be placed in the lower power, non-operating state (i.e., post-manufacture sleep mode). In this manner, the shelf life of the transmitter 102 may be significantly improved. Moreover, as shown in FIG. 2, while the power supply unit 207 is shown as coupled to the processor 204, and as such, the processor 204 is configured to provide control of the power supply unit 207, it should be noted that within the scope of the present invention, the power supply unit 207 is configured to provide the necessary power to each of the components of the transmitter unit 102 shown in FIG. 2.

Referring back to FIG. 2, the power supply section 207 of the transmitter 102 in one embodiment may include a rechargeable battery unit that may be recharged by a separate power supply recharging unit (for example, provided in the receiver unit 104 or in a mount to which the transmitter may be coupled, e.g., for on-body securement) so that the transmitter 102 may be powered for a longer period of usage time. Moreover, in one embodiment, the transmitter 102 may be configured without a battery in the power supply section 207, in which case the transmitter 102 may be configured to receive power from an external power supply source (for example, a battery) as discussed in further detail below.

Referring yet again to FIG. 2, the temperature detection section 203 of the transmitter 102 is configured to monitor the temperature of the skin near the sensor insertion site. The temperature reading may be used to adjust the glucose readings obtained from the analog interface 201. The RF transmitter 206 of the transmitter 102 may be configured for operation in the frequency band of about 315 MHz to about 470 MHz, for example, in the United States. Further, in one embodiment, the RF transmitter 206 is configured to modulate the carrier frequency by performing Frequency Shift Keying and Manchester encoding. In one embodiment, the data transmission rate is 19,200 symbols per second, with a minimum transmission range for communication with the receiver 104.

Referring yet again to FIG. 2, also shown is a leak detection circuit 214 coupled to the guard electrode (G) 211 and the processor 204 in the transmitter 102 of the data monitoring and management system 100. The leak detection circuit 214 in accordance with one embodiment of the present invention may be configured to detect leakage current in the sensor 101 to determine whether the measured sensor data are corrupt or whether the measured data from the sensor 101 is accurate.

Additional detailed description of the continuous glucose monitoring system, its various components including the functional descriptions of the transmitter are provided in U.S. Pat. No. 6,175,752 issued Jan. 16, 2001 entitled "Analyte Monitoring Device and Methods of Use", and in application Ser. No. 10/745,878 filed Dec. 26, 2003 entitled "Continuous Glucose Monitoring System and Methods of Use", and elsewhere.

Figure 3:
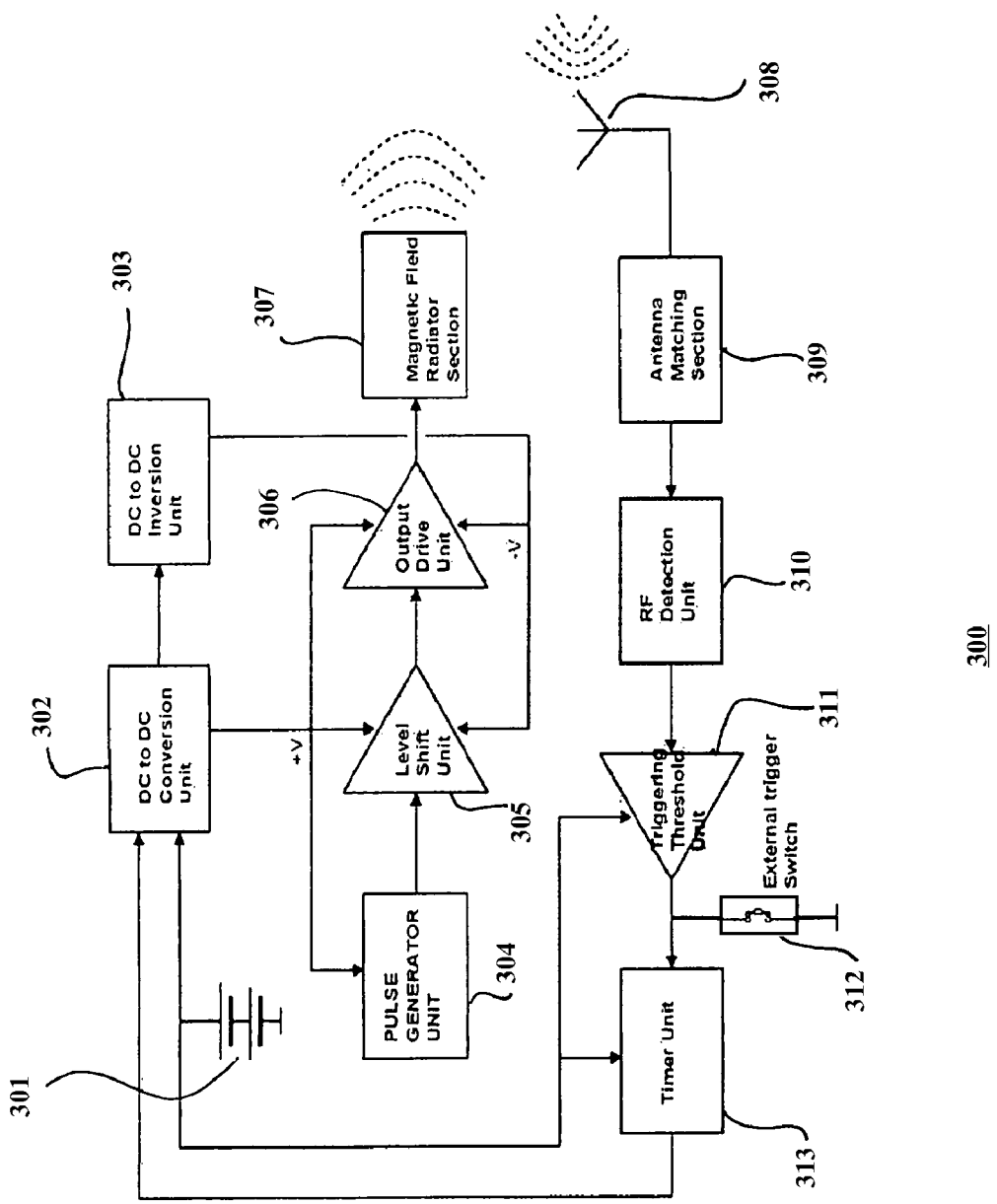
FIG. 3 is a block diagram of a magnetic field generator unit of the receiver unit configured for providing inductive power recharge in the data monitoring and management system in accordance with one embodiment of the present invention.

FIG. 3 is a block diagram of a magnetic field generator unit of the receiver unit (or other component) configured for providing inductive power recharge in the data monitoring and management system in accordance with one embodiment of the present invention. Referring to FIG. 3, the magnetic field generator unit 300 includes a power source such as a battery 301 configured to provide DC power to the magnetic field generator unit 300. Also shown in FIG. 3 is a DC to DC conversion unit 302 operatively coupled to the power source 301 and a DC to DC inversion unit 303. The magnetic field generator unit 300 in one embodiment also includes a pulse generator unit 304 operatively coupled to a level shift unit 305 which is in turn, operatively coupled to an output driver unit 306.

Referring again to FIG. 3, the output driver unit 306 is operatively coupled to a magnetic field radiation section 307 which, as described in further detail below, may be configured to generate and radiate a magnetic field. Also shown in FIG. 3 is an RF receiver antenna 308 which is configured to receive data from the transmitter unit 102 (FIG. 1) over the communication link 103 (FIG. 1). Additionally, referring still to FIG. 3, the RF receiver antenna 308 is operatively coupled to an antenna matching section 309 which in turn, is operatively coupled to an RF detection unit 310 which maybe configured to rectify the received RF signal from the transmitter unit 103 as discussed in further detail below. In addition, the RF detection unit 310 as shown in FIG. 3 is operatively coupled to a triggering threshold unit 311. The triggering threshold unit 311 is also operatively coupled to an external trigger switch 312 and a timer unit 313. In one embodiment, the timer unit 313 is operatively coupled to the power source 301 and the DC to DC conversion unit 302, and may be configured to control power supply in the magnetic field generator unit 300 to preserve power consumption and effectively conserve the life of the power source 301.

In one embodiment, the power source 301 is configured to provide direct current (DC) power supply for the magnetic field generator unit 300 that is provided in the receiver unit 104 (FIG. 1) of the data monitoring and management system 100. Alternatively, the magnetic field generator unit 300 may be incorporated into a separate unit or component and used to charge the power supply of the transmitter unit 102.

Referring back to FIG. 3, the DC to DC conversion unit 302 in one embodiment includes a step up DC to DC converter which is configured to boost the voltage level of the power source 301 to a higher positive DC voltage for the pulse generator unit 304, the level shift unit 305, and the output driver unit 306. The DC to DC inversion unit 303 in one embodiment may include a step up DC to DC inverter configured to boost the positive DC voltage received from the DC to DC conversion unit 303 to a negative DC voltage to increase signal swing dynamic range between the positive and negative power supply rails for the level shift unit 305 and the output drive unit 306.

Referring still to FIG. 3, the pulse generator unit 304 in one embodiment includes a square wave generator and configured to generate square wave signals from, for example, approximately 100 KHz to approximately 1 MHz and to provide the generated square wave signals to the level shift unit 305. The frequency range specified above may vary depending upon the specific component used and other design considerations. With the received square wave signals, the level shift unit 305 in one embodiment is configured to convert the positive square wave signals into corresponding positive and negative swing square wave signals with doubled voltage amplitude, which is provided to the output drive unit 306. The output drive unit 306, in turn, is configured to drive the magnetic field radiation section 307 by applying the full swing square wave signals from the level shift unit 305. In one embodiment, as discussed in further detail below in conjunction with FIG. 4, the magnetic field radiation section 307 includes a serial inductor-capacitor (LC) resonance circuit that may includes tuning capacitors and multilayered printed circuit board (PCB) core coil inductor.

Referring yet again to FIG. 3, the RF receiver antenna 308 in one embodiment is configured to receive the RF signals from the transmitter unit 102 (which may be associated with monitored or detected analyte levels received from the sensor unit 101 (FIG. 1)). In one embodiment, the resonance frequency of the RF receiver antenna 308 may be tuned at the same frequency of the RF carry signal from the transmitter unit 103. The antenna matching circuit 309 is configured to receive the RF signals from the RF receiver antenna 308, and to deliver the received energy from the RF receiver antenna 308 to the RF detection unit 310. In one aspect, the RF detection unit 310 maybe configured to use a zero bias or biased RF Schottkey barrier diode to rectify the amplitude envelope of the received RF signals from the RF receiver antenna 308.

Referring yet still to FIG. 3, the rectified signal from the RF detection unit 310 is provided to the triggering threshold unit 311 which, in one embodiment includes a voltage comparator that compares the signal amplitude level of the rectified signal from the RF detection unit 310 and a reference voltage. Thereafter, the triggering threshold unit 311 in one embodiment is configured to switch the output of the triggering threshold unit 311 to low logical level when the signal level from the RF detection unit 310 exceeds the reference voltage. Similarly, an external trigger switch 312 may be provided which is configured to pull down the output voltage of the triggering threshold unit 311 to a low logical level when the external trigger switch 312 is activated. In one embodiment, the external trigger switch 312 is provided to allow the user to manually turn on the magnetic field generator unit 300.

The triggering threshold unit 311 may be coupled to the timer unit 313 which in one embodiment includes a mono-stable timer, and may be configured to be triggered by the triggering threshold unit 311 to turn on or turn off the magnetic field generator 300 automatically and conserve the battery life of the power source 301. More specifically, in one embodiment, the timer unit 313 may be programmed to a time period that is longer than one time interval between two received RF signals from the transmitter unit 102, but which is shorter than two time intervals, such that the magnetic field generator unit 300 is configured to be turned on continuously when the RF signals are received by the RF receiver antenna 308.

In this manner, in one embodiment of the present invention, the magnetic field generator unit 300 may be configured to inductively charge the rechargeable power source of the transmitter unit 102 (FIG. 1). More specifically, when the transmitter unit 102 is positioned in close proximity to the magnetic field generator unit 300 (for example, incorporated into the receiver unit 104), the magnetic field generator unit 300 may be configured to activate automatically or manually depending upon the transmitter unit 102 transmission status.

That is, in one embodiment, when the transmitter unit 102 is transmitting RF signals, these signals received by the receiver unit 104 including the magnetic field generator unit 300 will activate the magnetic field generator unit 300 as described above by the RF receiver antenna 308 providing the received RF signals to the RF detection unit 310 via the antenna matching section 309. The rectified amplitude envelope signals from the RF detection unit 310 is then configured to pull down the output voltage of the triggering threshold unit 311 to a low logical level. The low logical level starts the mono stable timer unit 313, which turns on the DC to DC conversion unit 302 and for the pulse generator unit 304, the level shift unit 305, and the output drive unit 306 to generate the magnetic field which is then used to inductively recharge the power source in the transmitter unit 102.

In this manner, the RF signal transmission from the transmitter unit 102 in one embodiment is configured to maintain the magnetic field generator unit 300 to continuously generate the magnetic field, or alternatively, the trigger switch 312 may be activated to manually trigger the magnetic field generator unit 300 to continuously generate the magnetic field to inductively recharge the power supply of the transmitter unit 102.

Figure 4:
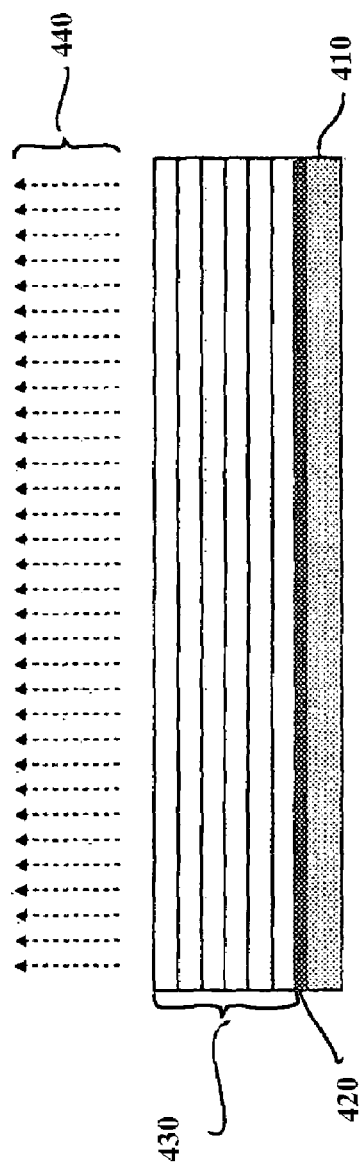
FIG. 4 illustrates the magnetic field radiation unit of the serial resonant tank section of the receiver unit shown in FIG. 3 in accordance with one embodiment of the present invention.

FIG. 4 illustrates the magnetic field radiation section 307 shown in FIG. 3 in accordance with one embodiment of the present invention. Referring to FIG. 4, the magnetic field radiation section 307 of FIG. 3 in one embodiment includes a flexible ferrite layer 410 having disposed thereon an adhesive layer 420 on which, there is provided multilayered PCB core coil inductor 430. In this manner, when the magnetic field generator unit 300 (FIG. 3) is activated, the magnetic field 440 is generated as shown by the directional arrows in FIG. 4. The flexible ferrite layer 410 increases the permeability of the PCB core coil inductor 430 by confining the bottom magnetic field in close proximity to the magnetic field radiation section 307. For a given coil inductor, the inductance is proportional to the permeability of the core material. Furthermore, since Q factor of the inductor is proportional to inductance of the inductor, in one embodiment, the Q factor and inductance of the multilayered PCB core coil inductor 430 are increased by the present of the flexible ferrite layer 410. Moreover, the resonance voltage and current developed on the multilayered PCB core coil inductor 430 is proportional to the Q factor. The magnetic field is, therefore, enhanced.

Figure 5:
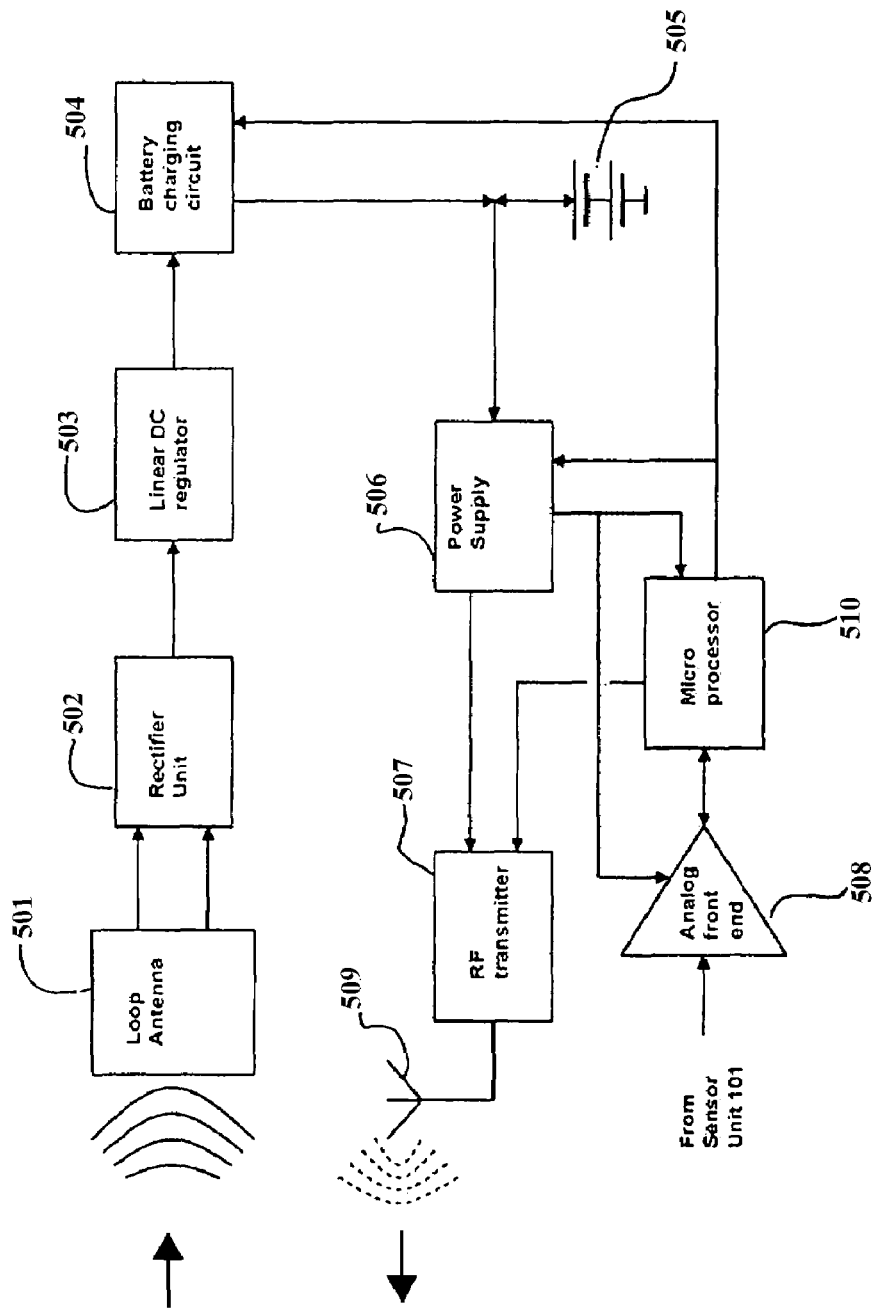
FIG. 5 is a block diagram illustrating the transmitter unit with a rechargeable battery configured for inductive recharging in the data monitoring and management system in accordance with one embodiment of the present invention.

FIG. 5 is a block diagram illustrating the transmitter unit with a rechargeable battery configured for inductive recharging in the data monitoring and management system in accordance with one embodiment of the present invention. Referring to FIG. 5, the transmitter unit 102 with inductive power recharge capability includes an antenna 501 which in one embodiment includes a parallel resonant loop antenna configured to resonate at the same frequency as the magnetic field generated by the magnetic field generator unit 300 (FIG. 3). The generated magnetic field 440 (FIG. 4) induces a current flow in the antenna 501 of the transmitter unit 102 when the transmitter unit 102 is positioned in close proximity to the magnetic field generator unit 300 (for example, when the transmitter unit 102 is placed on top of the magnetic field generator unit 300). The induced current flow then builds up AC voltage across the two ends of the loop antenna 501.

Referring back to FIG. 5, also shown is a rectifier unit 502 which, in one embodiment includes a full bridge rectifier, and is configured to rectify the AC voltage built up in the loop antenna 501 into a corresponding DC voltage. In turn, a linear DC regulator unit 503 is provided to convert the varying DC voltage from the rectifier unit 502 into a constant voltage which is provided to a battery charging circuit 504. The battery charging circuit 504 in one embodiment is configured to provide a constant charging current to charge a rechargeable battery 505 provided in the transmitter unit 102. Accordingly, in one embodiment, the rechargeable battery 505 may be configured to store the energy from the battery charging circuit 504 to provide the necessary power to drive the circuitry and components of the transmitter unit 102.

As shown in FIG. 5, an RF antenna 509 is coupled to an RF transmitter 507 which, under the control of a microprocessor 510 is configured to transmit RF signals that are associated with analyte levels monitored by an sensor unit 101 and processed by an analog front end section 508 which is configured to interface with the electrodes of the sensor unit 101 (FIG. 1). A power supply 506 is optionally provided to provide additional power to the transmitter unit 102.

Figure 6:
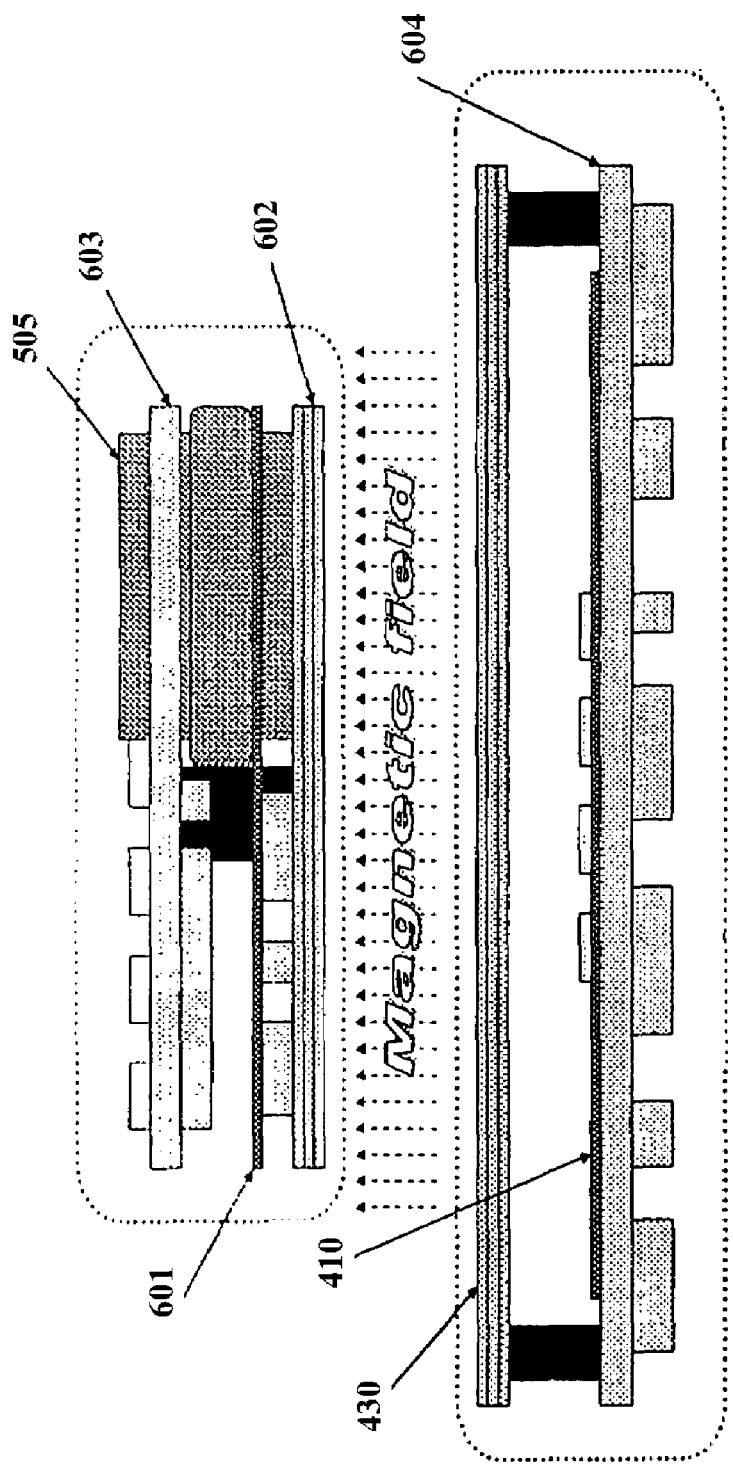
FIG. 6 is a function illustration of the high frequency power transformer of the transmitter unit and the receiver unit including the magnetic field generator unit of the data monitoring and management system in accordance with one embodiment of the present invention.

FIG. 6 is a function illustration of the high frequency power transformer of the transmitter unit and the receiver unit including the magnetic field generator unit of the data monitoring and management system in accordance with another embodiment of the present invention. Referring to FIG. 6, as can be seen, a high frequency power transformer is formed by the magnetic field radiation section 307 including the flexible ferrite layer 410 with the multilayered PCB core coil inductor 430 (for example, as similarly shown in FIG. 4), and a similar flexible ferrite layer 601 with a corresponding multilayered PCB core coil inductor 602 provided in the transmitter unit 102. The multilayered PCB core coil inductor 602 in one embodiment includes the loop antenna 501, the rectifier unit 502, and the linear DC regulator unit 503. As shown, when the transmitter unit 102 is positioned in close proximity to the magnetic field generator unit 300 of the receiver unit 104, for example, the high frequency power transformer is generated so as to inductively charge the rechargeable battery 505 of the transmitter unit 102.

Moreover, referring to FIG. 6, the circuit board 603 is configured in one embodiment to include the electronic components associated with the transmitter unit 102, for example, as discussed above in conjunction with FIGS. 2 and 5, while circuit board 604 is configured in one embodiment to include the electronic components associated with the receiver unit 104 including the magnetic field generator section 300. For example, in one embodiment, the circuit board 603 includes the power supply 506, the RF transmitter 507, the analog front end section 508, the RF antenna 509, and the microprocessor 510 as described above in conjunction with FIG. 5.

In the manner described above, in accordance with the various embodiments of the present invention, there are provided method and system for inductively recharging the power supply such as a rechargeable battery of a transmitter unit 102 in the data monitoring and management system 100 using a high frequency magnetic transformer that is provided on the primary and secondary printed circuit boards 603, 604 respectively. Accordingly, a significant reduction in size may be achieved in the transmitter unit 102 design and configuration which may be worn on the patient's body for an extended period of time. Moreover, since the transmitter unit power supply can be recharged without exposing the internal circuitry for example, using a battery cover to periodically replace the battery therein, the transmitter unit housing may be formed as a sealed enclosure, providing water tight seal.

In addition, within the scope of the present invention, the magnetic field generator may be integrated into a flexible arm cuff type device such that the power supply of the transmitter unit 102 may be recharged without being removed from its operating position on the skin of the patient or user, such that the contact between the electrodes of the sensor unit 101 and the transmitter unit 102 analog front end section may be continuously maintained during the active life cycle of the sensor unit 101.

Accordingly, an apparatus for providing rechargeable power for use in a data communication system in accordance with one embodiment of the present invention includes a power source section including a magnetic field generator unit configured to generate a magnetic field, and a rechargeable power section including a rechargeable power supply unit, wherein the rechargeable power supply unit is configured to be recharged when the rechargeable power section is provided in a predetermined proximity to the generated magnetic field of the power source section.

In one aspect, the power source section and the rechargeable power section may comprise a power transformer unit, which may include a high frequency power transformer.

The magnetic field generator unit may include a first coil inductor, and further, where the rechargeable power supply unit may include a second coil inductor, where also, each of the first and second coil inductors may include a plurality of PCB layers.

The rechargeable power section in one embodiment may include a data transmission unit, and further, wherein the power source section includes a data receiver unit, where the data transmission unit may be configured to transmit one or more signals to the data receiver unit in the rechargeable power section over a wireless communication link including an RF communication link.

In one embodiment, the magnetic field generator unit may be configured to be controlled by one or more of the transmitted signals from the data transmission unit.

An apparatus for providing rechargeable power for use in a data communication system in accordance with another embodiment of the present invention includes a power source section including a magnetic field generator unit configured to generate a magnetic field, a power section that is rechargeable provided in a predetermined proximity to the generated magnetic field of the power source section.

The power section may include a rechargeable power supply unit configured to be inductively recharged by the power source section.

In another aspect, a data transmitter unit may be configured to transmit one or more signals associated with an analyte level, the data transmitter unit including the power section.

In yet another aspect, a data receiver unit may be configured to receive one or more signals associated with an analyte level, the receiver unit including the power source section.

In still another aspect, a glucose monitoring system may be provided including a data transmitter unit configured to transmit one or more signals associated with an analyte level, and a data receiver unit configured to receive the one or more signals from the transmitter unit, wherein the transmitter unit includes the power section, and further, where the receiver unit including the power source section.

An analyte monitoring system with rechargeable power supply in accordance with another embodiment of the present invention includes an analyte sensor at least a portion of which is configured for subcutaneous placement under a skin layer, the sensor configured to detect an analyte level, a data transmission unit operatively coupled to the analyte sensor, the data transmission unit configured to transmit a plurality of signals including a signal associated with the detected analyte level, the data transmission unit further including a rechargeable power supply unit, and a data monitoring unit configured to receive the signal from the data transmission unit, the data monitoring unit further including a magnetic field generator unit, where the rechargeable power supply unit is configured to be recharged by the magnetic field generator unit.

In one aspect, the magnetic field generator unit may be configured to inductively charge the rechargeable power supply unit.

Further, the magnetic field generator unit may include a first multilayered coil inductor, and the rechargeable power supply unit may include a second multilayered coil inductor, where a first ferrite layer may be disposed on the first multilayered coil inductor, and a second ferrite layer may be disposed on the second multilayered coil inductor.

Moreover, the magnetic field generator unit maybe configured to be controlled by one or more of the transmitted signals from the data transmission unit.

In another aspect, the magnetic field generator unit may be configured to generate a magnetic field, and where the rechargeable power supply unit may be configured to be recharged by the magnetic field generator unit when the data transmission unit is positioned in a predetermined proximity to the magnetic field.

Also, the magnetic field generator unit may be configured to generate a power transformer between the data transmission unit and the data monitoring unit.

A method of providing rechargeable power supply in accordance with yet another embodiment of the present invention includes generating a magnetic field, positioning a rechargeable power source within a predetermined distance from the generated magnetic field, and inductively charging the rechargeable power source. In certain embodiments, the method is a method of providing power to a transmitter of a transmitter of an analyte monitoring system.

In one aspect, generating the magnetic field may be triggered by the RF data transmission detection.

Also, the method may further include manually controlling the step of generating the magnetic field.

Moreover, in a further aspect, the method may also include detecting one or more analyte levels of a patient, and transmitting one or more signals associated with the detected one or more analyte levels.

In addition, the method may also include receiving the transmitted one or more signals, and/or monitoring an analyte level of a patient, where the analyte level includes a glucose level.

Various other modifications and alterations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments. It is intended that the following claims define the scope of the present invention and that structures and methods within the scope of these claims and their equivalents be covered thereby.

What is claimed is:

1. A system, comprising:
   an analyte sensor;
   a control unit;
   a power source section including a magnetic field generator unit configured to generate a magnetic field, the power source section coupled to the control unit and configured to generate the magnetic field in response to one or more control signals from the control unit; and
   a rechargeable power section that is rechargeable provided in a predetermined proximity to the generated magnetic field of the power source section;
   wherein the one or more control signals provided to the power source section to generate the magnetic field is associated with a monitored analyte level from the analyte sensor.

2. The system of claim 1 wherein the power source section and the rechargeable power section comprise a power transformer unit.

3. The system of claim 2 wherein the power transformer unit includes a high frequency power transformer.

4. The system of claim 1 wherein the magnetic field generator unit includes a first coil inductor, and further, wherein the rechargeable power section includes a second coil inductor.

5. The system of claim 4 wherein each of the first and second coil inductors includes a plurality of printed circuit board (PCB) layers.

6. The system of claim 1 wherein the rechargeable power section includes a data transmission unit, and further, wherein the power source section includes a data receiver unit.

7. The system of claim 6 wherein the data transmission unit is configured to transmit one or more signals to the data receiver unit in the rechargeable power section over a wireless communication link.

8. The system of claim 7 wherein the wireless communication link includes a radio frequency (RF) communication link.

9. The system of claim 7 wherein the one or more control signals is configured to activate the magnetic field generator unit to generate the magnetic field in response to the transmitted signals associated with the monitored analyte level from the data transmission unit.

10. The system of claim 1 wherein the rechargeable power section includes a rechargeable power supply unit configured to be inductively recharged by the power source section.

11. The system of claim 1 further including a data transmitter unit configured to transmit one or more signals associated with an analyte level, the data transmitter unit including the rechargeable power section.

12. The system of claim 1 further including a data receiver unit configured to receive one or more signals associated with an analyte level, the receiver unit including the power source section.

13. The system of claim 1 further including a glucose monitoring system, the glucose monitoring system including a data transmitter unit configured to transmit one or more signals associated with the analyte level, and a data receiver unit configured to receive the one or more signals from the transmitter unit, wherein the transmitter unit includes the rechargeable power section, and further, wherein the receiver unit includes the power source section.

14. An analyte monitoring system with rechargeable power supply, comprising:
an analyte sensor at least a portion of which is configured for subcutaneous placement under a skin layer, the sensor configured to detect an analyte level;
a data transmission unit operatively coupled to the analyte sensor, the data transmission unit configured to transmit a plurality of signals including a signal associated with the detected analyte level, the data transmission unit further including a rechargeable power supply unit; and
a data monitoring unit configured to receive the signal from the data transmission unit, the data monitoring unit further including a magnetic field generator unit and a control unit coupled to the magnetic field generator unit, the magnetic field generator unit configured to generate a magnetic field in response to one or more control signals from the control unit;
wherein the rechargeable power supply unit is configured to be recharged by the magnetic field generator unit; and further
wherein the control unit is configured to generate the one or more control signals in response to the received signal associated with the detected analyte level from the data transmission unit.

15. The system of claim 14 wherein the magnetic field generator unit is configured to inductively charge the rechargeable power supply unit.

16. The system of claim 14 wherein the magnetic field generator unit includes a first multilayered coil inductor, and further, wherein the rechargeable power supply unit includes a second multilayered coil inductor.

17. The apparatus of claim 16 further including a first ferrite layer disposed on the first multilayered coil inductor, and a second ferrite layer disposed on the second multilayered coil inductor.

18. The apparatus of claim 14 wherein the data transmission unit is configured to transmit the plurality of signals to the data monitoring unit over a radio frequency (RF) communication link.

19. The apparatus of claim 14 wherein the magnetic field generator unit is configured to be controlled by one or more of the transmitted signals from the data transmission unit.

20. The apparatus of claim 14 wherein the magnetic field generator unit is configured to generate a magnetic field, and further, wherein the rechargeable power supply unit is configured to be recharged by the magnetic field generator unit when the data transmission unit is positioned in a predetermined proximity to the magnetic field.

21. The apparatus of claim 14 wherein magnetic field generator unit is configured to generate a power transformer between the data transmission unit and the data monitoring unit.

22. A method of providing rechargeable power supply, comprising:
receiving a signal associated with a monitored analyte level from an analyte sensor;
generating a magnetic field in response to the received signal;
positioning a rechargeable power source within a predetermined distance from the generated magnetic field, the rechargeable power source operatively coupled to the analyte sensor; and
inductively charging the rechargeable power source.

23. The method of claim 22 wherein generating the magnetic field is triggered by radio frequency (RF) data communication detection of the received signal associated with the monitored analyte level.

24. The method of claim 22 further including manually controlling the magnetic field generation.

25. The method of claim 22 wherein the analyte level includes a glucose level.

* * * * *

UNITED STATES PATENT AND TRADEMARK OFFICE
CERTIFICATE OF CORRECTION

PATENT NO. : 7,620,438 B2  Page 1 of 1
APPLICATION NO. : 11/396135
DATED : November 17, 2009
INVENTOR(S) : Lei He It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 559 days.

Signed and Sealed this

Twenty-sixth Day of October, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,620,438 B2 | Page 1 of 1 |
| APPLICATION NO. | : 11/396135 | |
| DATED | : November 17, 2009 | |
| INVENTOR(S) | : Lei He | |

It is certified that error appears in the above-identified patent and that said Letters Patent is hereby corrected as shown below:

ON THE TITLE PAGE:

In Item (57), Abstract, line 5, replace "rechargeable rower source" with --rechargeable power source--.

Signed and Sealed this

Seventh Day of February, 2012

David J. Kappos
*Director of the United States Patent and Trademark Office*